US006843942B2

(12) United States Patent
Katinger et al.

(10) Patent No.: US 6,843,942 B2
(45) Date of Patent: Jan. 18, 2005

(54) METHOD AND DEVICE FOR PRODUCING LIPID VESICLES

(75) Inventors: Hermann Katinger, Vienna (AT); Karola Vorauer-Uhl, Vienna (AT); Andreas Wagner, Baden (AT); Guenter Kreismayr, Vienna (AT)

(73) Assignee: Polymun Scientific Immunobilogische Forschung GmbH, Vienna (AT)

( * ) Notice: Subject to any disclaimer, the term of this patent is extended or adjusted under 35 U.S.C. 154(b) by 0 days.

(21) Appl. No.: 10/415,414

(22) PCT Filed: Oct. 31, 2001

(86) PCT No.: PCT/EP01/12595

§ 371 (c)(1),
(2), (4) Date: Aug. 28, 2003

(87) PCT Pub. No.: WO02/36257

PCT Pub. Date: May 10, 2002

(65) Prior Publication Data

US 2004/0032037 A1 Feb. 19, 2004

(30) Foreign Application Priority Data

Nov. 3, 2000 (EP) .............................................. 00123953

(51) Int. Cl.[7] ................................................ B01J 13/02
(52) U.S. Cl. .......................... 264/4.1; 264/4.33; 425/5; 425/7; 428/402.2
(58) Field of Search ................................ 264/4.1, 4.33; 425/5, 7; 428/402.2

(56) References Cited

U.S. PATENT DOCUMENTS

| 4,206,197 A | 6/1980 | Goldberg |
| 4,895,452 A | 1/1990 | Yiournas et al. |
| 5,000,887 A | 3/1991 | Tenzel et al. |
| 5,834,016 A | 11/1998 | Naeff et al. |

FOREIGN PATENT DOCUMENTS

| EP | 0 253 619 | 1/1988 |
| WO | WO 00/29103 | 5/2000 |

OTHER PUBLICATIONS

Batzri, S., et al., "Single Bilayer Liposomes prepared without sonication", *Biochimica et Biophysica Acta*, 298 (1973) 1015–1019.

Kremer, J.M.H., et al., "Vesicle of Variable Diameter Prepared by a Modified Injection Method", *Biochemistry*, vol. 16, No. 17, 1977, 3932–3935.

Kriftner, R., "Liposome production: the ethanol injection technique and the development of the first approved liposome dermatic", *Liposome Production: The Ethanol Injection Technique*, 91–100.

Naeff, R., "Feasibility of topical liposome drugs produced on an industrial scale", *Advanced Drug Delivery Reviews*, 18 (1996) 343–347.

*Primary Examiner*—Samuel A. Acquah
(74) *Attorney, Agent, or Firm*—Rothwell, Figg, Ernst & Manbeck, PC

(57) ABSTRACT

The invention relates to a device for producing lipid vesicles, which is equipped with a line (1) for transporting a polar liquid phase, with a line (2) for transporting an organic liquid phase containing lipids, with a collecting receptacle (7) for accommodating produced lipid vesicles, and with means for conveying the liquid phases through lines (1) and (2). At at least one location, the outer side of line (1) forms a common contact surface with line (2) inside of which a common opening (3) is provided that permits the flow of liquid and joins the inside of line (2) to the inside of line (1). Lines (1) and (2) do not contain agitating or dispersing aids in the area of the opening (3). The invention also relates to a method for the careful production of lipid vesicles, wherein the lipid phase is sprayed under pressure perpendicular to the direction of flow of the polar phase and into the same, whereupon lipid vesicles having a narrow size distribution form spontaneously and without the action of mechanical agitating or dispersing aids.

25 Claims, 9 Drawing Sheets

METHOD AND DEVICE FOR PRODUCING LIPID VESICLES

The invention relates to a process and an apparatus for the particularly mild production of vesicles, in particular lipid vesicles, on the laboratory scale and industrial scale. The invention furthermore relates to the vesicles and vesicular preparations produced by means of this process.

PRIOR ART

The prior art discloses numerous different vesicular preparations. They comprise both pure lipid vesicles, also referred to as liposomes, and lipid vesicles which are provided with cell-specific markers, such as, for example, antibodies or antibody fragments, in particular Fab' and F(ab')$_2$, and are generally referred to as immunoliposomes, or lipid vesicles which are provided with viral coat proteins or surface antigens, for example haemagglutinin, and are usually referred to as virosomes. In addition, lipid vesicles which contain both viral antigens and specific marker molecules in the vesicle membrane have also been disclosed. The vesicles generally contain an aqueous phase, which in the simplest case may be pure water, aqueous buffer systems, such as, for example, PBS, or a physiological saline solution. For pharmaceutical and medical applications, including diagnostic applications, however, the vesicles generally contain one or more desired substances, for example a physiologically active substance, a drug, a specific marker or nucleic acid material.

The simplest and most widely used category of lipid vesicles are the liposomes. They are generally composed of phospholipids which form spontaneously into membrane structures when they are dispersed in aqueous systems. During this procedure, a part of the aqueous system is enclosed by these structures in the course of the vesicle formation. In practice, those liposomes whose vesicle membrane is in the form of a lipid bi-layer, like natural membranes, are generally preferred.

Since the first presentation of liposomes by Bangham in 1964 (J. Mol. Biol. 13:238–252, 1965), a number of different liposome preparation techniques have become established. These include processes in which lipids are mixed together with the desired active substance in a suitable aqueous solvent and then subjected to ultrasound, with the result that vesicles form. In other processes, for example according to Stegman et al. (EMBO Journal 6:2651–2659, 1987), the solvent is slowly removed by dialysis or by means of microcarriers, vesicles which enclose a part of the aqueous phase likewise forming spontaneously.

Known high pressure homogenization, microfluidizer and ultrasonic processes for the production of liposomes are distinguished by the use of the shear forces and cavitation effects occurring in the process, in order to obtain lipid vesicles of defined size. Cavitation effects lead locally to very high pressures and temperatures. Liposomes, in particular unsaturated fatty acid radicals of the lipids, can as a result be damaged by oxidation and thus change their stability. For this reason, antioxidants or other protective ingredients must be added to such processes and/or the entire process must be carried out in the absence of oxygen, for example in a nitrogen atmosphere, as described, for example, in EP 0 253 619 or U.S. Pat. No. 5,834,016. In these processes, the preparation of the lipid vesicles is carried out in a plurality of cycles.

Furthermore, large volumes of liposomes of defined size can be produced by so-called "extrusion". In the extrusion, prepared lipid membrane structures, for example commercially available large (>500 nm) liposomes, are pressed under high pressure through membranes of defined pore size and thus adjusted to the desired diameter. As in high pressure homogenization and ultrasonic methods, it is necessary to carry out a plurality of cycles in order to obtain a narrow size distribution of the end product. A possible disadvantage of this method consists in considerable product losses which occur through breaking open and reclosing of the vesicles in the course of passage through the membranes. Product losses of well over 50 percent can readily occur in this process, as our own comparative experiments have shown.

Another method which serves for spontaneous vesicle formation at the phase boundary from organic to inorganic phase is the solvent injection method. The self-assembly process (spontaneous arrangement of the lipids to form vesicles) takes place during the injection of the lipids dissolved in an organic phase into a vigorously stirred aqueous (or other suitable polar) phase, said injection being carried out using a fine needle. This method is very simple but has the major disadvantage that very inhomogeneous and large liposomes are produced at relatively high lipid concentrations. This method was described for the first time by Batzri and Korn (Biochimica et Biophysica Acta, 298:1015–1019, 1973).

EP 253 619 describes a process according to the last-mentioned solvent injection method, in which an organic phase containing dissolved lipids is injected under pressure into a high-speed homogenizer and is dispersed therein by vigorous stirring, with strong turbulences, into an aqueous phase, whereupon liposomes are formed. A possible disadvantage of this method is that strong shear forces, cavitation and very considerable local temporary temperature increases are produced in the homogenizer. As a result of such effects, oxidation reactions of unsaturated fatty acid radicals and other undesired reactions can be initiated, which at least damage both lipids and substances or active substances sensitive to shear forces, oxidation or temperature, and in certain circumstances may even make them unsuitable for further use.

A similar process is also described in U.S. Pat. No. 4,895,452, in which multi- or paucilamellar vesicles are produced in a separate mixing chamber into which the liquid streams of the polar and the lipid-containing phases are injected tangentially in order thus to achieve shear forces which are as high as possible and thorough mixing.

Furthermore, WO 00/29103 discloses a process in which lipid vesicles are produced from a lipid-containing and an aqueous liquid stream by suitable mixing means and with the use of high shear forces.

In contrast, the present invention, which is substantially a further development of the solvent injection method, no longer has the disadvantages of the known processes but makes it possible, in an extremely mild preparation procedure, to establish a narrow size distribution of liposomes of a desired size in a controlled manner. In addition, the process according to the invention permits continuous operation and a simple scale-up for the industrial production of germ-free and/or pyrogen-free lipid vesicle preparations, but also a scale-down for microproduction, i.e. the production of very small amounts of lipid vesicles, for example for the purpose of scientific research.

SUMMARY OF THE INVENTION

It is an object of the invention to provide a process for the particularly mild production of lipid vesicles, which can be scaled up or scaled down, is in particular continuous, gives homogeneously distributed vesicle preparations in a reproducible manner and, in a preferred embodiment, permits the production of germ-free and/or pyrogen-free vesicle preparations.

The present invention also comprises the liposomes which can be prepared or are prepared by this process and the cosmetic or pharmaceutical products based on these liposomes and their use for cosmetic, medical and/or diagnostic purposes.

Contrary to the known ethanol injection method, the polar, as a rule aqueous, phase according to the present invention is pumped from a storage container into a pipe system connected thereto and comprising one or more pipes. Each pipe through which the polar phase flows and which leads away from the storage container contains, at a predetermined point, at least one, very exactly designed, laterally arranged hole or orifice, optionally a plurality of said holes or orifices, which is or are connected through the pipe wall and on the outside to at least one feed pipe, optionally a plurality of said feed pipes, for the pressure-controlled feeding of the lipid phase dissolved in a suitable solvent, in particular ethanol.

In contrast to the classical ethanol injection method, however, there is in the apparatus according to the invention no injection needle which extends into the aqueous phase; instead, the at least one feed pipe for the lipid phase ends, according to the invention, at the at least one hole or orifice of the pipe system leading away from the storage container and intended for the aqueous phase, so that no obstacles or barriers generating turbulences or shear forces project into the interior of the pipes. As a result of the pressure-controlled feeding of the lipid phase into the polar/aqueous phase flowing past with preferably laminar flow, the desired lipid structures form, in the region of contact of the two phases, through a controllable self-assembly effect, into vesicles of uniform size and narrow size distribution not achievable to date.

Surprisingly and completely unexpectedly, it has also been found that, in the method according to the invention, neither relatively high lipid concentrations nor relatively high ethanol concentrations appear to influence the vesicle formation and the distribution of the vesicle sizes. This to some degree contradicts the prevailing opinion of persons skilled in the art that the vesicle formation is dependent on the lipid concentration, the ethanol concentration, the flow rates of the aqueous and the organic phase and the stirring speed of the homogenizing apparatus.

According to the present invention, neither ultrasound nor homogenizer is required for vesicle formation or for establishing the desired vesicle size. The filtration process ("extrusion process") known from the prior art for establishing a vesicle size which is as uniform as possible can also be advantageously replaced by the present invention. According to the invention, the vesicle size and size distribution can in fact be controlled in particular via the metering pressure, the higher the metering pressure of the lipid phase fed in, the smaller the vesicles and the sharp or narrower the size distribution of the resulting lipid vesicles in the natural lipid vesicle preparation, even at high lipid concentrations.

By means of the process according to the invention, it is possible to enclose in liposomes not only water-soluble active substances but also those which are initially taken in the organic phase and are introduced together with the lipids into the aqueous system, such as, for example, those as disclosed in EP 0 253 619 or U.S. Pat. No. 5,834,016. In these cases, the aqueous system may be water, physiological saline solution, PBS or any desired, suitable buffer. The substances initially taken in the organic, substantially non-polar phase are either completely or partly integrated into the lipid bi-layer during the formation of the lipid vesicles or become closely associated with said bi-layer through lipophilic interactions. It is also possible initially to take desired substances or active substances and to load liposomes therewith in both phases, i.e. both in the polar and in the organic, lipid-containing phase.

In the present process, both a batchwise and a continuous procedure can be chosen. In the batchwise procedure, a predetermined volume of polar phase is circulated in the system, i.e. recycled into the starting vessel and loaded again with lipid-containing phase. By supplying the lipid-containing phase, the polar solution gradually becomes enriched with lipid vesicles. In the continuous process, the polar phase is not recirculated but, after metering of the lipid-containing phase and the spontaneous vesicle formation are complete, it is collected as vesicle suspension in an external collecting container. The vesicle sizes or size distributions of the two vesicle suspensions are not influenced by the different process modes.

In a further development of the continuous process, first polar buffer phase is initially taken in the external collecting container and, secondly, the otherwise usual amount of lipid fed in (and preferably also of organic solvent) per unit volume of polar/aqueous phase flowing past is increased by two to ten times. Consequently, the volumetric product yield (amount of liposomally incorporated, preferably active substance-containing, polar phase) can be increased proportionally to the amount of lipid phase fed in. Where the substances to be liposomally incorporated are lipophilic and are initially taken together with the lipids in the organic phase, a one hundred percent or at least approximately one hundred percent yield is also achievable without recirculation, i.e. the total or virtually the total amount of initially taken desired substance, for example a drug, is subsequently contained in the lipid vesicles.

The vesicle sizes and size distributions described herein were determined by means of flow cytometry, adapted according to Vorauer-Uhl et al., Cytometrie 39(2):166–71 (2000). In this method, in contrast to conventional static or dynamic laser light scattering, the vesicles are measured individually in a capillary system (10,000 vesicles per measurement). By means of this method, both homogeneous and heterogeneous vesicle populations can be reliably characterized.

According to the invention, the polar phase and the lipid-containing phase are transported separately from one another and fed to a phase intersection region which is preferably in the form of a cross-flow module. The lipid-containing phase flows into the likewise flowing, polar phase via at least one laterally arranged orifice in the pipe system of the polar phase, preferably inside the cross-flow module. The lipid vesicles formed when the two phases come into contact with one another are either recycled together with the polar (e.g. aqueous) phase into the starting container or transported further into a collecting container. The lipid vesicles form spontaneously in the phase intersection region, i.e. in the region where the polar and the lipid-containing phases come into contact with one another. In order very substantially to avoid cavitation effects and/or shear forces and associated local temperature increases, the liquid stream, at least of the polar phase, is preferably passed as far as possible with laminar flow to the orifice or the orifices. In the case of particularly sensitive substances or mixtures, it may be advantageous to strive for low-shear flow behaviour of the resulting phase dispersion also downstream of the intersection region of the phases.

In contrast to the known lipid/ethanol injection methods, according to the present invention the liquid in the intersection region of the phases is neither stirred nor is a homogenizer or another mechanical stirring or dispersing aid used. The feeding of the lipid-containing phase into the polar/aqueous phase is effected under relatively low pressure and hence with little eddy formation, the lipid phase presumably emerging as a sort of spray mist from the pipe orifice and interacting very rapidly with the polar phase. By regulating the feed rates and flow rates of both the polar and the lipid-containing phases and by varying the metering pressure for feeding in or "spraying in" the lipid-containing phase, the self-assembly process of the lipid vesicles is controllable. With increasing metering pressure, the lipid vesicles forming become smaller and at the same time their size distribution becomes narrower.

With the aid the present invention, lipid vesicle preparations can be produced on different production scales—from experimental or laboratory sizes to industrial dimensions. Since the vesicle formation takes place continuously not in a stirred vessel but in a key component of the pipe system, preferably in the cross-flow module mentioned, preparations of uniform and reproducible quality with respect to product inclusion rate, vesicle size and vesicle size distribution are always produced, independently of the chosen production scale, in the production according to the invention when the substantial process parameters, such as metering pressure of the lipid-containing phase, flow volume of the polar phase, flow ratio of polar to lipid-containing phase and lipid concentration of the lipid-containing phase, are kept constant. With the choice of appropriate pipe cross-sections and/or an increase in the number and/or in the diameter of the orifice(s) in the pipe system of the polar phase, it is also possible to adapt the throughput volume flexibly to different production specifications.

The production principle also makes it possible at least partly to circulate the phase dispersion forming in the phase intersection region, e.g. in the cross-flow module, and to feed it, optionally several times in succession, back to the phase intersection region and to load it with lipid-containing phase.

The inclusion rate (degree of utilization) of the substances dissolved in the polar phase into the lipid vesicles can also be increased by increasing the volume fraction of the lipid-containing phase and introducing larger volumes of lipid-containing phase per unit time into the stream of the polar solution. Downstream of the phase intersection region, the phase dispersion formed can be diluted with a polar solvent, for example with the carrier medium of the polar phase, in order—if required—to increase the stability of the liposome preparation.

The present invention also comprises an apparatus for the production of lipid vesicles. It consists in principle of a first storage container for the polar phase and a separate, second storage container for the substantially nonpolar lipid-containing phase; a collecting container for receiving the vesicle preparation produced; a pipe system which leads from the first storage container (polar phase) to the collecting container and which has a defined, laterally arranged orifice or hole for entry of the lipid-containing phase at at least one point of the or each pipe; a further pipe system which leads from the second storage container (lipid-containing phase) to at least one of these lateral orifices or holes of the first pipe system; and means for producing the required liquid streams, flow profiles and pressures for the controlled transport of the phases and of the resulting phase dispersion.

Preferably, that part of the pipe system for the polar phase which has the at least one lateral orifice and that part of the pipe system for the lipid-containing phase which is connected thereto are present in a cross-flow module which may be an industrially prefabricated unit which can be easily and rapidly integrated as a connecting key component into the pipe system of the two phases. It is preferable if, at least inside this cross-flow module, the feed pipes for the polar and the lipid-containing phases consist of stable and chemically resistant material, for example of stainless steel or rigid plastic, and are connected to one another tightly and in a nonslippable manner, for example by welding. For batchwise or semicontinuous operation, the first storage container can moreover simultaneously act as a collecting container, at least a part of the pipe system leading away from the storage container being led in a loop and opening again into the storage container so that at least a part of the polar phase is circulated and is recycled, including newly formed lipid vesicles, into the storage container/collecting container.

DETAILED DESCRIPTION OF THE PREFERRED EMBODIMENTS

Figure 1A:
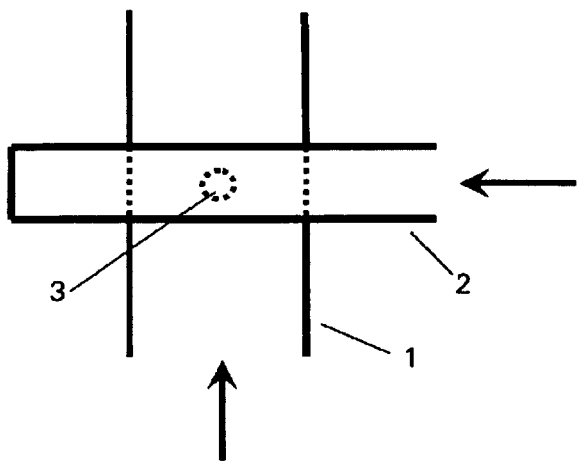
FIG. 1A shows a schematic diagram (in plan view) of a cross-flow module comprising a liquid pipe for the polar phase (shown vertically) and a lateral feed pipe for the lipid-containing phase (shown horizontally); flow directions are indicated by arrows.

Aqueous systems, for example pure water, PBS (phosphate-buffered, physiological saline solution), physiological saline solution or another suitable and pharmaceutically acceptable buffer, optionally with customary additives, such as preservatives, fragrances, colorants and the like, are preferably used as carrier medium of the polar phase, both for cosmetic and pharmaceutical preparations, in particular those for medical applications.

The carrier medium of the lipid-containing phase is preferably selected from those nontoxic, pharmaceutically acceptable, organic solvents or solvent mixtures which are suitable for dissolving the lipids or lipid mixtures chosen for the respective intended use and the optionally additional substances. Such additional substances may be, for example, viral, fusogenic peptides, such as, for example, influenza haemagglutinin, or cell-specific markers, such as, for example, antibody fragments, or lipophilic active substances, such as, for example, econazole or the like. Preferred solvents are lower alcohols (1–6 carbon atoms), such as methanol, ethanol, n-propanol, isopropanol and n-butanol, it being possible to use these solvents individually, as a mixture and/or optionally together with a suitable buffer.

The lipid vesicles of the present invention are not limited to specific lipids or lipid compositions. Depending on the intended use, they can contain simple and/or complex lipids, in particular phospholipids, glycolipids, derivatized lipids, and other natural or synthetic lipids of a cationic, anionic and/or neutral nature. Such lipids are known in the prior art. Lipoproteins or lipopolysaccharides can also be incorporated into the membrane of the lipid vesicles by the production method according to the invention. Membrane-stabilizing agents, such as cholesterol or cholesterol derivatives or polyethylene glycol and its derivatives, can be added.

The term "lipid vesicle" as meant in the context of the present invention comprises both pure lipid vesicles formed exclusively from lipids and also referred to as liposomes, and lipid vesicles which are provided with cell-specific markers, for example cytokines, growth hormones, antibodies or antibody fragments, and frequently referred to as immunoliposomes, or lipid vesicles which are provided with viral proteins or antigens, for example haemagglutinin, and usually referred to as virosomes. In addition, lipid vesicles may contain both viral antigens and specific markers in the vesicle membrane.

Here, "natural lipid vesicle preparation" is to be understood as meaning a lipid vesicle suspension which has formed only by virtue of the polar and lipid-containing phases coming into contact with one another according to the invention, under conditions with low shear forces or free of shear forces, directly and without the action of additional aids, such as, for example, ultrasound or mechanical stirring or dispersing aids, and—with the exception of any subsequent dilution with a polar solvent—has not been subjected to any further aftertreatment, in particular has not been subjected to any aftertreatment for establishing a desired vesicle size or vesicle size distribution.

"Desired substance" means any chemical substance or compound with which lipid vesicles can be loaded, the substance either adhering to the outside of the vesicle membrane and/or being integrated into the vesicle membrane and/or being enclosed in the interior of the lipid vesicle and being capable of being brought in vitro and/or in vivo with the aid of the lipid vesicle to a desired destination. This substance can be any test substance, for example for scientific purposes, or a pharmaceutically active substance, a medicamentous active substance, a placebo, a substance for cosmetic purposes, a marker, a radiolabelled or fluorescence labelled compound for therapeutic or diagnostic applications, another chemical compound or mixture of chemical compounds.

Figure 1B:
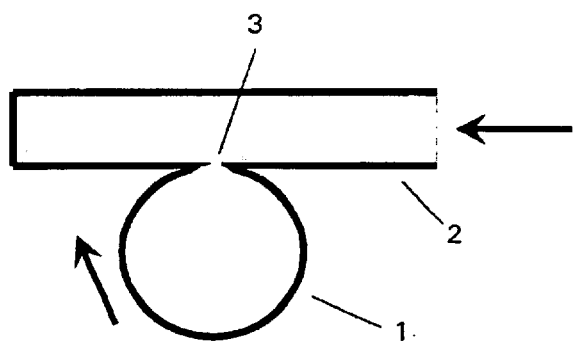
FIG. 1B shows a cross-sectional view of the cross-flow module of FIG. 1A.
Figure 1C:
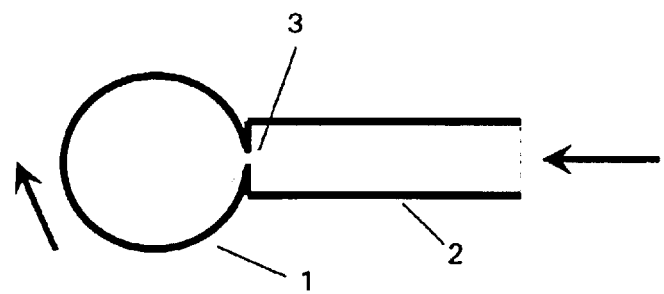
FIG. 1C shows a cross-sectional view of a cross-flow module with T-shaped arrangement of the feed pipes for the polar and lipid-containing phases.

The principle of the polar (e.g. aqueous) phase and the lipid phase coming into contact with one another, on which the invention is based, is shown schematically in FIG. 1A, FIG. 1B and FIG. 1C. A liquid pipe 2 which is hollow in the interior and transports the organic lipid phase in the direction of a horizontal arrow is connected to the outside of a liquid pipe 1 which is likewise hollow in the interior and transports the polar (aqueous) phase. At least one hole or orifice 3 which extends through the side wall of the pipe 1 and through the adjacent side or end wall of the pipe 2 and produces a liquid-permeable connection between the interior of the pipe 1 and the interior of the pipe 2 is located in the region of the contact point between the two pipes. The pipe 2 may intersect the pipe 1 (cross-flow module), as shown schematically in FIGS. 1A and 1B, or may be tightly and nonslippably fastened, e.g. welded, with its end face directly to the side wall of the pipe 1, as shown schematically in FIG. 1C.

Figure 2:
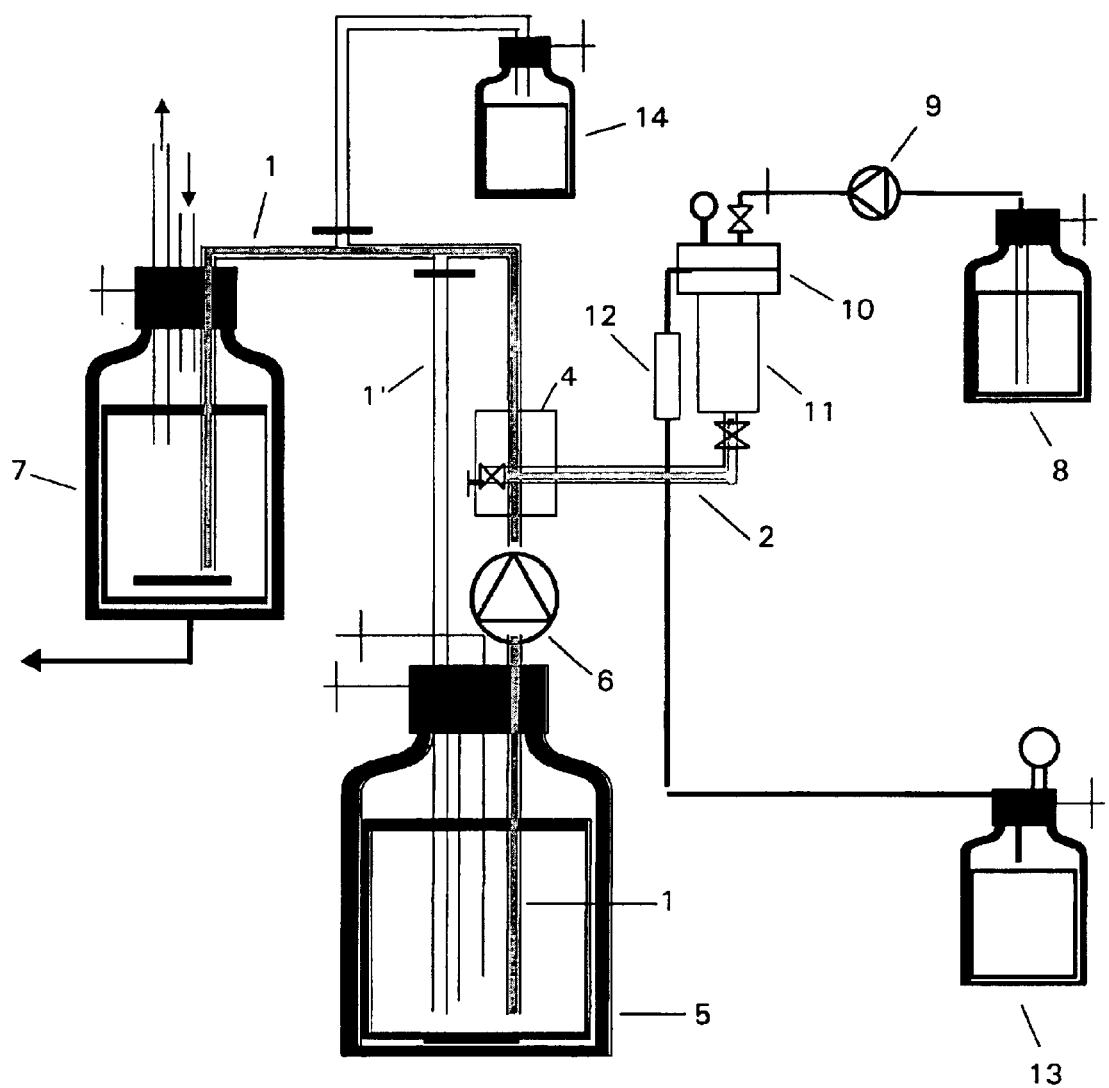
FIG. 2 shows a schematic diagram of the apparatus according to the invention for (e.g. continuous) operation without recycling of the polar phase or phase dispersion.
Figure 3:
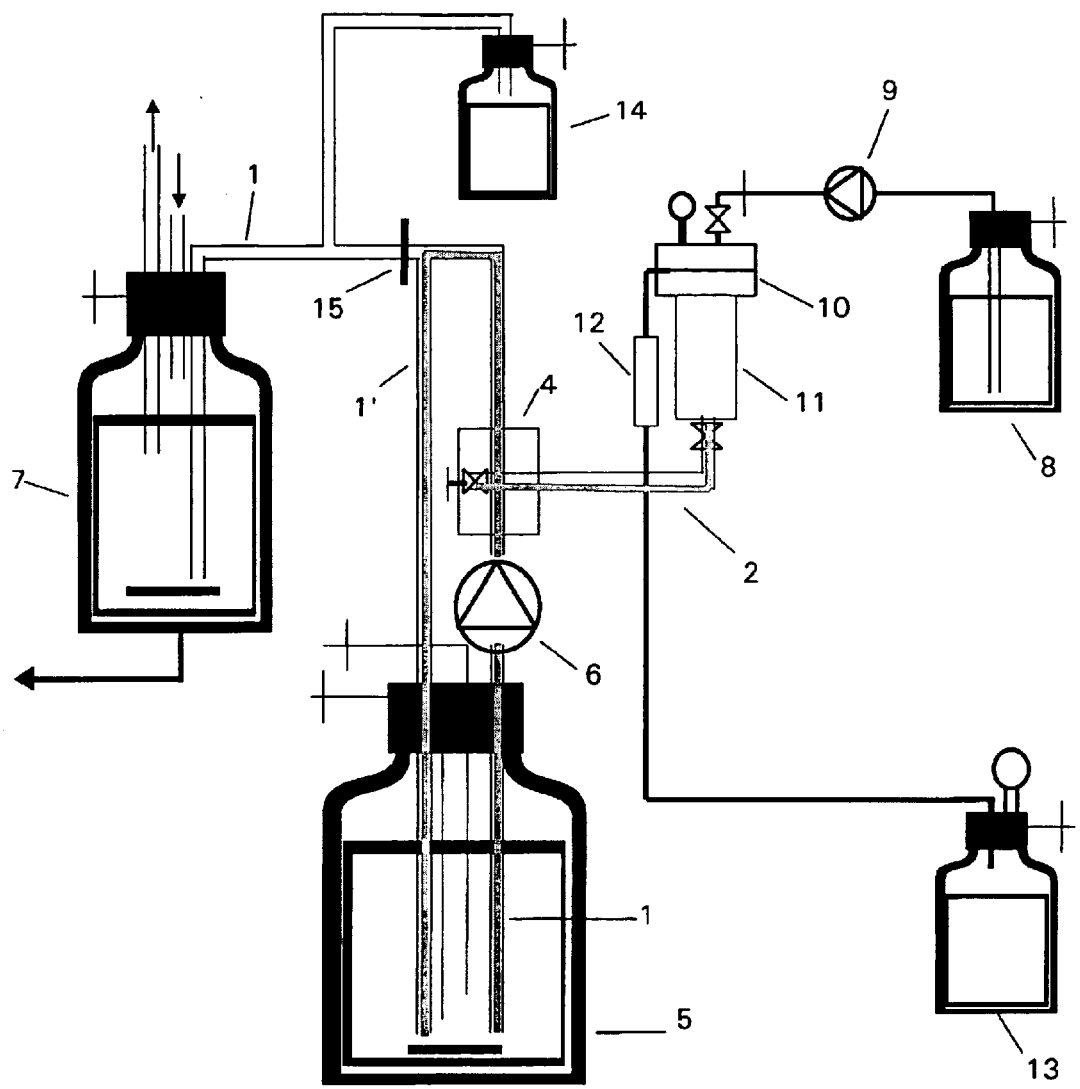
FIG. 3 shows a schematic diagram of the apparatus from FIG. 2 for (e.g. batchwise) operation with recycling of the polar phase or phase dispersion into the storage container.
Figure 4:
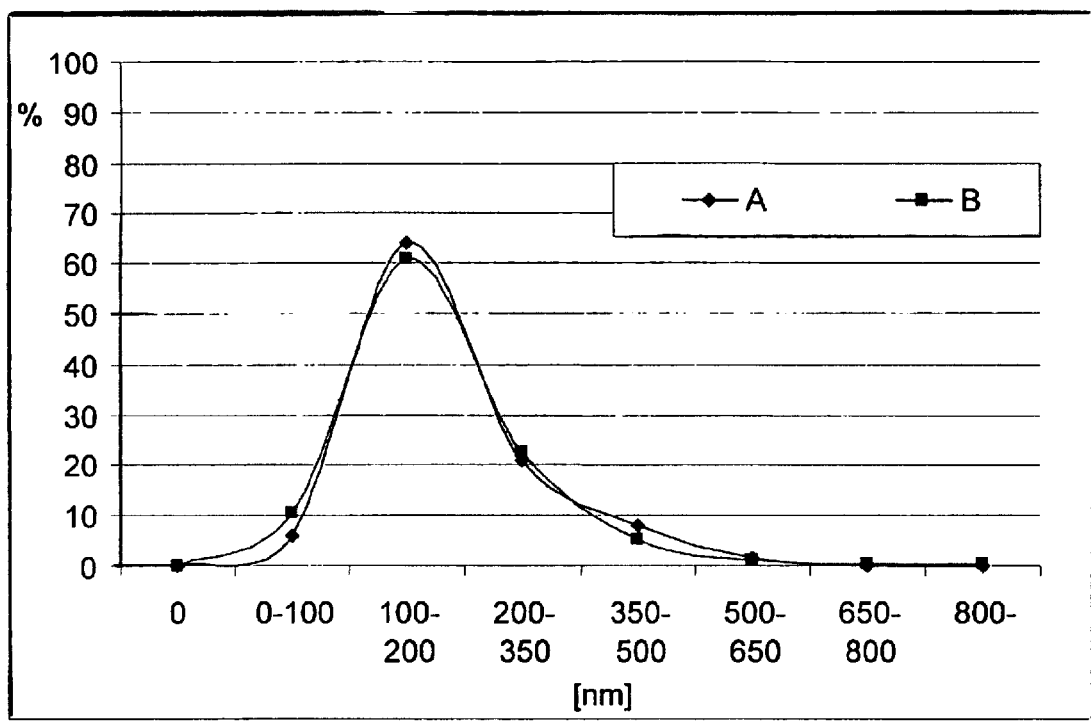
FIG. 4 shows size distributions of liposome preparations produced by the direct process without recycling (curve B) and by a circulatory process (curve A) with recycling of the phase dispersion into the starting container and subsequent further loading with lipid phase (ordinate: percent of lipid vesicle population; abscissa: diameter of the lipid vesicles in nm)
Figure 5:
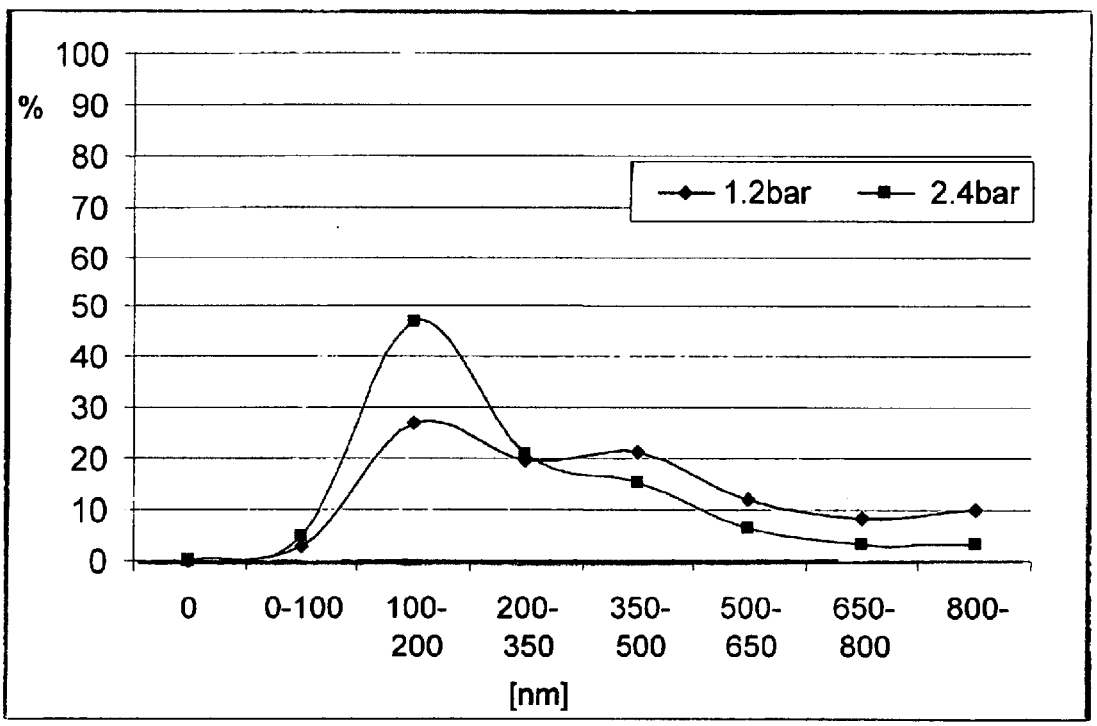
FIG. 5 and FIG. 5A show size distributions in liposome preparations (20 $\mu$mol DPPC/ml polar phase) prepared at different metering pressures (1.2 bar and 2.4 bar or 2.5 bar and 4.5 bar) of the lipid-containing phase (ordinate: percent of lipid vesicle population; abscissa: diameter of the lipid vesicles in nm)
Figure 5A:
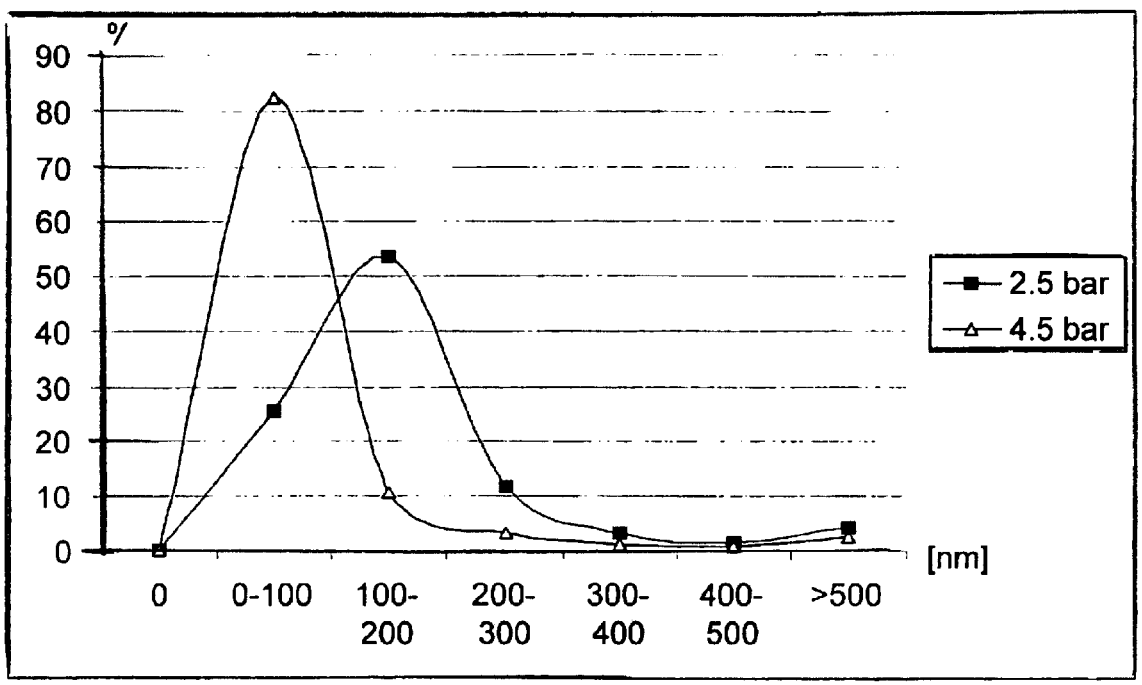
Figure 6:
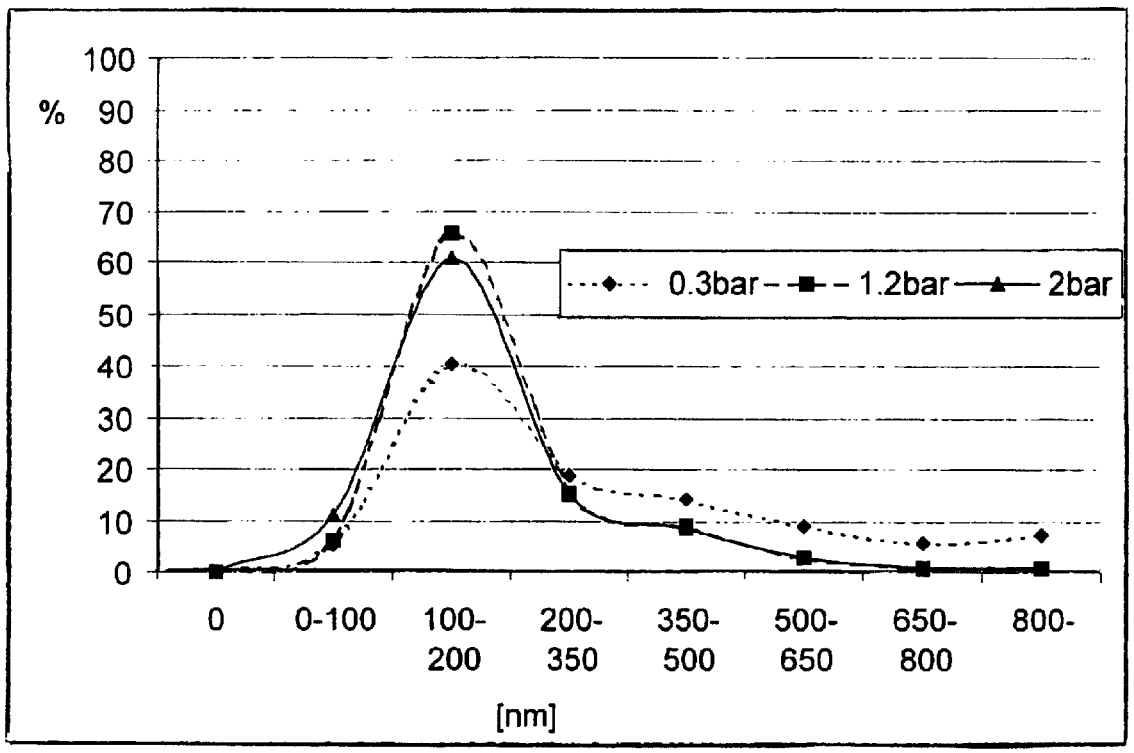
FIG. 6 shows size distributions of lipsome preparations (10 $\mu$mol DPPC/ml polar phase), prepared at different metering pressures (0.3, 1.2 and 2 bar) of the lipid-containing phase (ordinate: percent of lipid vesicle population; abscissa: diameter of the lipid vesicles in nm)

A key component of the present invention is an apparatus for the production of the lipid vesicles, as shown by way of example in FIG. 2 and FIG. 3. In a cross-flow module 4, a liquid pipe 2 (lipid phase) is connected to a pipe 1 (polar phase) so that they form a common contact surface with their outsides and are optionally superposed one on the other, the angle at which the two pipes are superposed or intersect being unimportant. In principle, they can also be arranged parallel to one another or T-shape with respect to one another and connected to one another, as shown, for example, in FIG. 1C. What is important, however, is that the two pipes have, in the region of their common contact surface, at least one common orifice 3, for example a hole, which connects the interiors of the two pipes 1 and 2 to one another and permits the passage of liquid. The lipid phase flowing through the pipe 2 is fed through the orifice 3 under moderate excess pressure of, preferably, 0.1 to 15 bar into the polar phase flowing past the orifice 3. The common orifice 3 is arranged so that the organic liquid phase from the pipe 2 can pass transversely, preferably substantially perpendicularly, to the direction of flow of the polar liquid phase flowing in the pipe 1, through the orifice 3, and, preferably in the form of a spray mist, can enter the polar liquid phase flowing past the orifice 3.

"Substantially perpendicularly" means that the feeding in or spraying in of the lipid phase takes place not in or against the direction of flow of the polar phase but transversely thereto at an angle, preferably a right angle, so that the lipid phase penetrates the flow of the polar liquid phase from the side, i.e. from the outer edge, towards the centre. It also means that, where a spray mist characteristic is present, as shown schematically in FIGS. 1A to 1C, only a part of the lipid phase sprayed in actually enters the polar phase at right angles to the direction of flow of the polar phase, while the predominant part deviates therefrom to a greater or lesser extent. In the region of the common orifice 3, the pipes 1 and 2 are free of additional means, in particular freed of stirring or dispersing aids.

FIG. 2 shows, by way of example, an arrangement of the apparatus according to the invention for carrying out a continuous or semicontinuous production process for lipid vesicles, without recycling of the resulting vesicle suspension into the starting container. Since this method of production substantially comprises a single process step, namely the combination of the lipid phase and the polar phase, this process is also referred to below as a "one-stage process".

The polar phase is transported from a first storage container 5 by means of a pump 6 which preferably operates with as little pulsation as possible and generates as little cavitation and shear forces as possible, through the liquid pipe 1 in the direction of the cross-flow module 4 and further into the collecting container 7, the pump 6 being arranged between the storage container 5 and the cross-flow module 4. During operation, the pump 6 is preferably set so that laminar or virtually laminar flow is present in the pipe 1 between the storage container 5 and the collecting container 7, at least at close range before and after the orifice 3. It is also preferable to ensure that no air bubbles are enclosed in the pipe 1, which air bubbles might reduce the yield of intact vesicles and hence the degree of enclosure of active substance from the polar phase. On passing through the cross-flow module 4, the polar phase is loaded with the organic, lipid-containing phase, the lipid-containing phase being fed in under pressure through the orifice 3, substantially at right angles to the direction of flow of the polar phase. It is found that the lipids are precipitated inside the cross-flow module 4 itself and closed to form vesicles, said lipids enclosing a part of the polar phase together with any substances dissolved therein.

The volumes and flow rates of the lipid-containing and of the polar phase are preferably tailored to one another so that unused excesses of one of the two phases are very substantially avoided. The lipid-containing phase is pumped from a second storage container 8 by means of a pump 9 via a filter 10 and a nonreturn valve or other pressure-blocking valve into an intermediate container 11. In this example, the intermediate container 11 is connected via an intermediate filter 12 to a pressure source 13, for example a pressurized container, which preferably contains an inert gas, for example nitrogen gas, under pressure and with the aid of which the lipid-containing phase is forced from the intermediate container 11 via a controllable valve in the direction of the cross-flow module 4.

If, owing to the lipid composition and/or the choice of the liposomally enclosed substance, no protection from oxidation is required, compressed air can also be used. Alternatively, the lipid-containing phase can be transported by means of a pump from the intermediate container 11 via the pipe 2 to the cross-flow module 4. As soon as the polar phase passes the orifice 3 in the cross-flow module 4, a controllable valve in the pipe 2 is opened and the lipid-containing phase is forced or pumped through the orifice 3 into the pipe 1 and hence into the polar phase. For process control and quality control, a sampling apparatus 14 can also be provided downstream of the cross-flow module 4.

FIG. 3 shows the arrangement from FIG. 2, with recycling of the phase dispersions forming in the cross-flow module 4 into the first storage container 5 (circulation process). Downstream of the cross-flow module 4, at least a part of the phase dispersion is branched off through a gate 15, for example a valve, a slide valve, a clamp or the like, before the collecting container 7, recycled via a return pipe 1' into the first storage container 5 and passed by means of pump 6 back to the cross-flow module 4 where it is again loaded with lipid-containing phase. As soon as the desired final concentration of lipid or lipid vesicles in the polar phase is reached and/or the lipid-containing phase has been used up, the circulation is stopped and the phase dispersion formed is either transferred to the collecting container 7 or collected in the storage container 5. The apparatus according to the invention, as shown by way of example in FIGS. 2 and 3, can be operated in a germ-free and pyrogen-free manner by known methods of sterile technology. For example, it can be thermally or chemically sterilized and the starting materials (polar phase, lipid-containing phase, optionally compressed air or inert gas) can be fed via suitable sterile filter systems to the respective storage containers 5, 8, the cross-flow module 4 and the subsequent collecting container 7. The natural lipid vesicle preparations produced in this manner then no longer need to be subjected to any further disinfection step.

The size distribution inside the vesicle preparations is decisively influenced in the process according to the invention by two factors: first, by the amount of lipid and/or solvent metered in per part by volume of the polar phase and, secondly, by the metering pressure. FIG. 5 and FIG. 6 show that, by increasing the metering pressure, the mean diameter of the lipid vesicles decreases and the size distribution within the vesicle population shows less scatter and is hence more homogeneous. Under the process conditions of FIG. 6, for example, two thirds of all liposomes produced have a diameter of 100 to 200 nm. The difference between the process conditions of FIG. 5 and of FIG. 6 consists in particular in the amount of lipid used per unit volume of the polar phase. In FIG. 5 and FIG. 5A, 20 μmol of lipid were used per ml of polar phase, whereas only 10 μmol/ml were used in FIG. 6. It has been found that, at lower metering pressures, it is advantageous in the case of the chosen lipid composition (results in FIG. 4 to 11) to meter in not more than 10 μmol of lipid per ml of polar phase, in order to obtain homogeneous vesicle preparations having little scatter in the size distribution. By increasing the metering pressure, however, it is possible not only to increase the efficiency of the process but also to achieve a small scatter of the vesicles produced with increased amount of lipid (per unit volume of the polar phase) (FIG. 5A).

Figure 7:
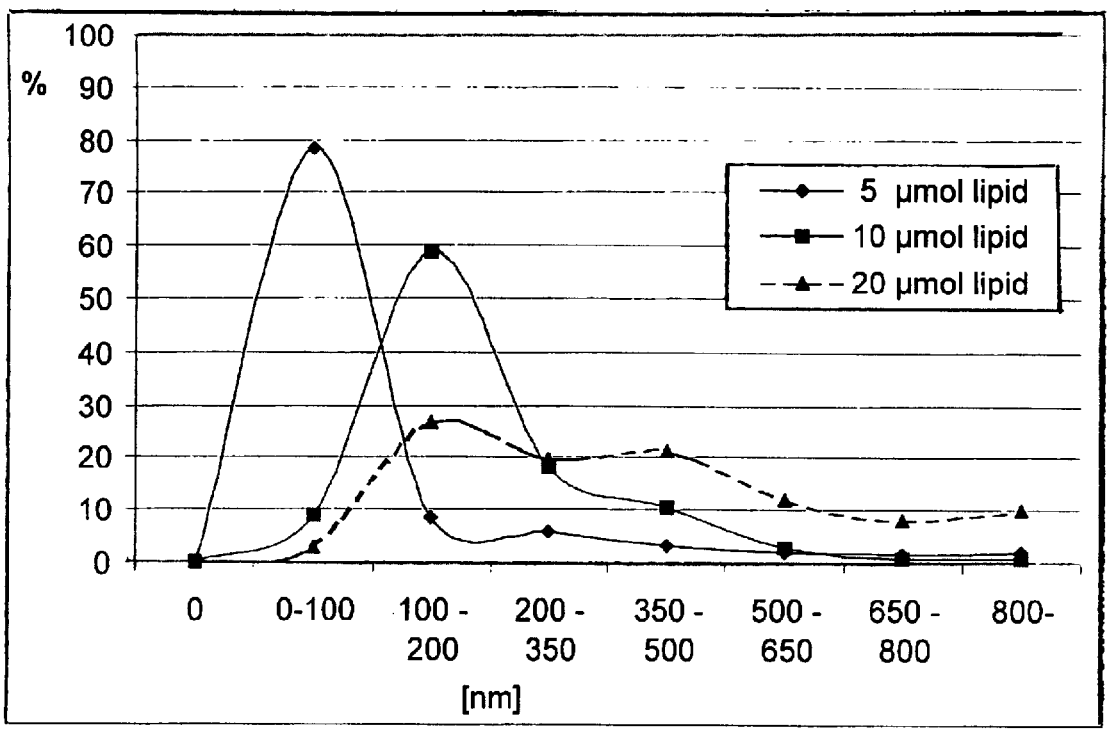
FIG. 7 shows the size distributions within liposome preparations as a function of the ratio of the amount of lipid used (in $\mu$mol) per part by volume (in ml) of the polar phase (5, 10 and 20 $\mu$mol/ml) used under otherwise constant conditions (ordinate: percent of lipid vesicle population; abscissa: diameter of the lipid vesicles in nm)
Figure 9:
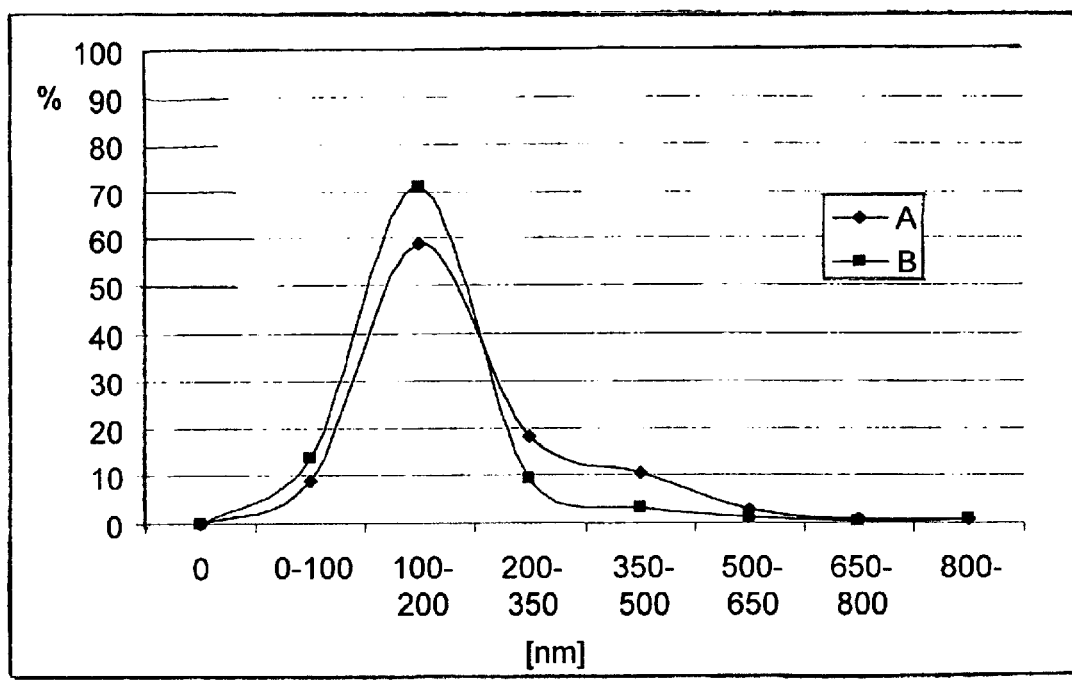
FIG. 9 shows a comparison of the size distribution of the lipid vesicles between a one-stage direct process (curve A) and a process (curve B) with an increased mixing ratio (metered volume of the lipid phase per unit volume of polar phase) and subsequent dilution of the phase dispersion (ordinate: percent of lipid vesicle population; abscissa: diameter of the lipid vesicles in nm)

FIG. 7 shows that, with increasing amount of lipid per unit volume of polar phase, expressed in μmol of lipid used per ml of polar phase used, the average size of the lipid vesicles and the scatter of the size distribution increase under constant conditions of the other process parameters. However, this effect can be counteracted by increasing the metering pressure of the lipid-containing phase so that, as shown in FIG. 9, an outstanding homogeneity and size distribution of the lipid vesicles nevertheless results in spite of considerable increase in the lipid fraction. A possible explanation for this phenomenon might be that, at higher metering pressures, the "spray mist" of the lipid-containing phase, which acts on the polar phase, is even finer and therefore has a larger surface. Moreover, the depth of penetration of the "spray mist" into the polar phase is also likely to be increased so that the observed, reproducible, phenomenon can be derived from all of this. Comparative experiments have in any case shown that the above-mentioned lipid effect could not be eliminated by varying the flow rate of the polar phase. The best values with respect to homogeneity of the vesicles were achieved with lipid concentrations of 10 μmol/ml or lower, at least with the use of DPPC as the sole bi-layer-forming lipid component.

It is furthermore preferred to choose the volume of the organic phase to be metered in, in the case of ethanol as a solvent, so that the calculated final concentration of ethanol (with the use of ethanol having a purity ≧90% by volume) in the vesicle dispersion present downstream of the cross-flow module 4 does not exceed 10% by volume, preferably 7.5% by volume. Exceeding the final concentration can adversely affect the stability, homogeneity and size of the resulting lipid vesicles in the collecting container 7. In the case of macromolecules, such as, for example, proteins, degrees of inclusion of 10 to 15% by weight of the total amount of the added macromolecule dissolved in the aqueous phase are achievable under these conditions of the one-stage process (without recycling).

However, a considerable increase in yield can be achieved by means of a preferred embodiment of this process. There, the mixing ratio of lipid-containing phase metered in to polar phase flowing past is adjusted to a value which far exceeds the above-mentioned preferred limits of 7.5% by volume of ethanol and 10 μmol of lipid per 1 ml of the polar phase in the vesicle dispersion, for example by two to ten times. The highly concentrated vesicle suspension can then be diluted with a polar solvent, preferably with the carrier medium of the polar phase, to the desired final concentration of 7.5–10% by volume of ethanol, in order—if required—to ensure the stability and homogeneity of the preparation also for a longer period (for example for storage purposes). The dilution can already be effected in the pipe 1 downstream of the cross-flow module, or only in the collecting container 7.

It has been found that in this way the degree of inclusion could be increased several times over, in particular for proteins. Thus, by increasing the metered volume of the lipid phase three-fold, a directly proportional increase in the degree of inclusion by likewise about three times, for example from 10–15% by weight of recombinant h-SOD to 30–50% by weight of rh-SOD, could be achieved. An increase in the mixing ratio to five to ten times the limits preferred in the unmodified process could give a further increase in the yield, resulting in a degree of utilization which approximately corresponded to the theoretically possible one. What is important here, however, is that the lipid vesicles produced retain the characteristic size distribution, as evident, for example, in FIG. 9, in spite of the increased mixing ratio, something which was by no means originally to be expected or foreseen.

Figure 10:
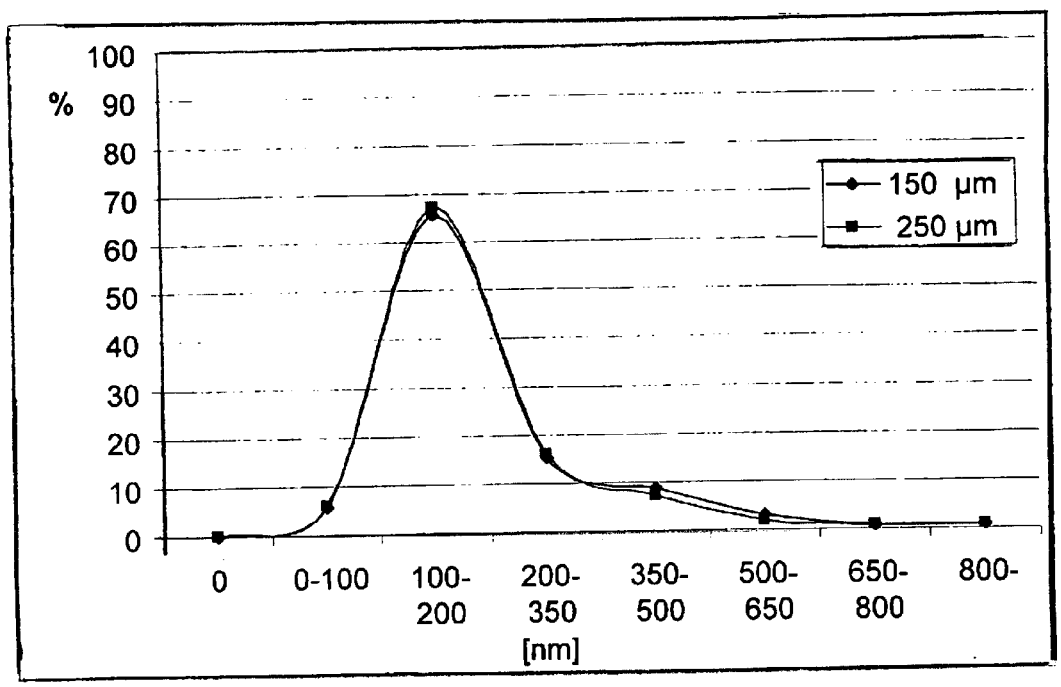
FIG. 10 shows the size distribution of the lipid vesicles in two liposome preparations, prepared using cross-flow modules with holes of 150 and 250 $\mu$m diameter (ordinate: percent of lipid vesicle population; abscissa: diameter of the lipid vesicles in nm)
Figure 11:
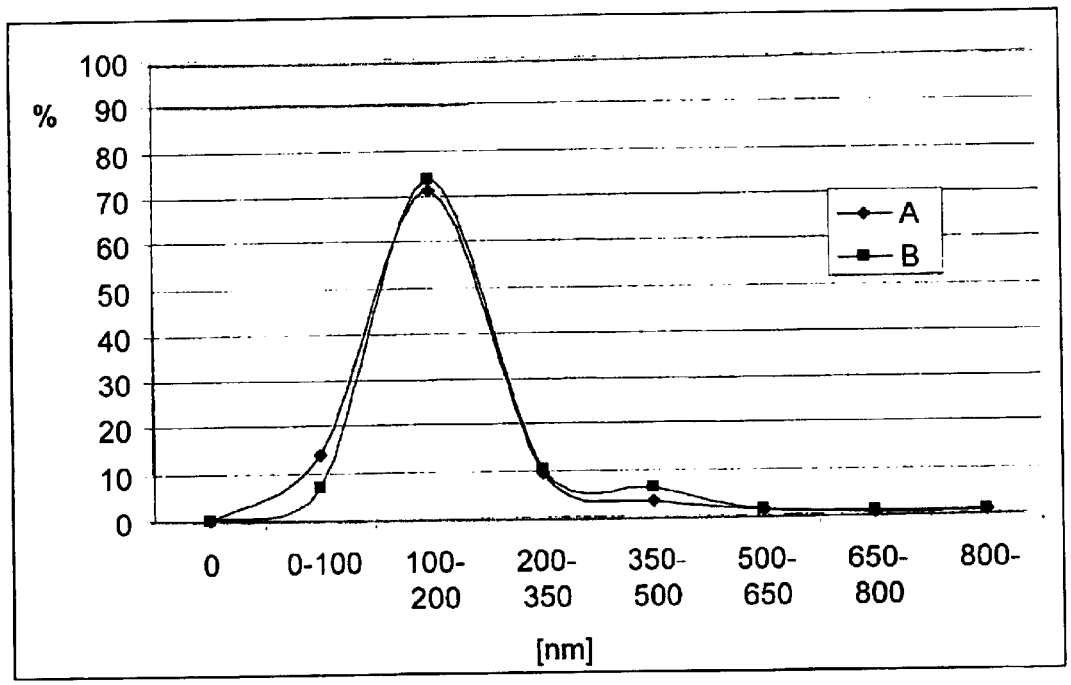
FIG. 11 shows the size distribution of the lipid vesicles in two liposome preparations, prepared using cross-flow modules (250 $\mu$m hole) with a production volume of 0.3 l (curve A) and a production volume of 2.5 l (curve B) (ordinate: percent of lipid vesicle population; abscissa: diameter of the lipid vesicles in nm)

The increase in the mixing ratio can be effected by increasing the metering pressure of the lipid phase and optionally additionally by increasing the diameter of the orifice 3 and/or by increasing the number of orifices 3. It is also possible to divide the feed stream of the lipid phase and to connect two or more pipes 2 to the pipe 1 via contact areas of the orifices 3. The experiments have shown that a change of (increase) in the hole diameter of the orifice 3 from, for example, 150 to 250 μm permits a considerable increase in the throughput of ethanolic phase (FIG. 12) but evidently does not have any substantial effect on the average size or size distribution of the lipid vesicle (FIG. 10). Depending on the intended use, it is therefore also possible to choose other diameters of the orifice 3. Diameters in the range of 50–1500 μm have proven to be suitable. It is of course also possible and, particularly for production purposes on a relatively large scale, advantageous to divide the liquid stream of the polar phase and to provide two or more pipes 1 in order thus to be able to increase the number of contact areas and orifices 3 even further.

Figure 13:
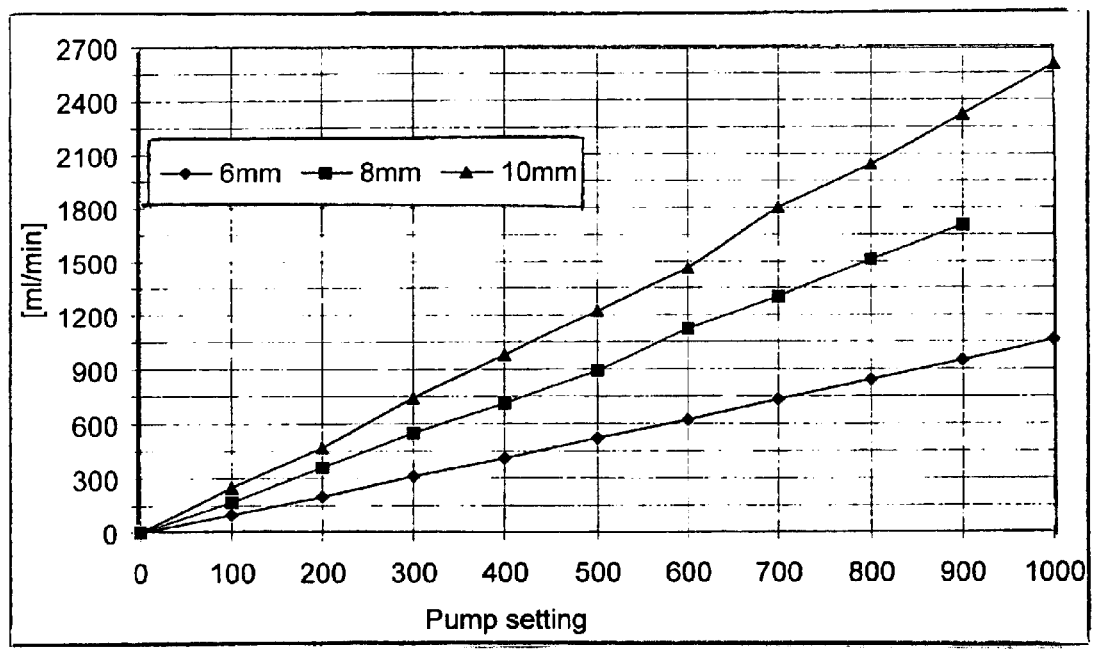
FIG. 13 shows flow rates of PBS as a polar phase with different pipe diameters (6, 8 and 10 mm; pump: peristaltic pump Ismatec SA0702 type).

For tailoring the volume flows and flow rates of the polar and of the lipid-containing phase to one another in a controlled manner, it is advantageous, in preceding experiments to measure the achievable flows as a function of the pump setting and the chosen pipe cross-sections and, as, for example, in FIG. 13, to plot them graphically for an apparatus on the laboratory scale. The process temperature for the vesicle production is of course dependent on the chemical nature of the lipids used and on the possible thermal sensitivity of the substance to be enclosed. However, it is always above the phase transition temperature of the lipids used.

By means of the process according to the invention, it is possible to produce, in a single process step, natural vesicular preparations in which at least 60% of all lipid vesicles (FIGS. 4–11), optionally more than 70% (FIG. 6) of all lipid vesicles, have a desired, predeterminable diameter which is within a scatter of not more than 250 nm, preferably of not more than 100 nm. The term "scatter" is understood in this context as meaning a size interval of said width within which the diameter of these at least 60 or 70% of all vesicles are distributed, i.e. "scatter". Accordingly, it is possible to produce vesicular preparations according to the invention in which at least 60% of all vesicles have a diameter in the range of, for example, 100–200 nm (scatter=100 nm) or at least 70% have a diameter in the range of 100–350 nm (scatter=250 nm). However, it is also possible to produce vesicular preparations in which at least 60% or at least 70% of all vesicles have a diameter in the range of 500–600 nm (scatter 100 nm) or 500–750 nm (scatter 250 nm). The process can be substantially adapted to the various needs of cosmetic, diagnostic or medical-therapeutic applications, both with respect to the desired lipid composition and with respect to the optimum vesicle size and the substances to be incorporated. Below, the invention is further explained with reference to examples.

EXAMPLE 1

Incorporation of Recombinant Human Superoxide Dismutase (rh-SOD) into Lipid Vesicles Recombinant human superoxide dismutase (rh-SOD) is a protein having a molecular weight of about 32000 Dalton.

WO 96/14083 reports in detail about the advantages of liposomal encapsulation of this protein and the medical applications thus permitted. Since this protein is dissolved in the polar phase and does not interact with the lipid membranes, the rh-SOD is "passively" incorporated.

One-stage process (shown schematically in FIG. 2): 1600 mg of rh-SOD are dissolved in 100 ml of PBS (115 mg of $Na_2HPO_4$, 20 mg of $KH_2PO_4$; 800 mg of NaCl; 20 mg of KCl, pH 7.2–7.4) as polar phase and 10 µmol/ml (based on the volume of the polar phase) of bi-layer-forming lipid, for example 734 mg of DPPC (dipalmitoylphosphatidylcholine), together with 2.86 µmol/ml (110 mg) of cholesterol and 1.43 µmol/ml (38.5 mg) of stearylamine, are dissolved in 7.5 ml of ethanol (concentration: 92% by volume) as organic phase. The lipid composition, in this case DPPC, cholesterol and stearylamine in the ratio of 7.2:1 µmol/ml, can, however, vary both with respect to the choice of the lipid components and with respect to the ratios of the lipid components to one another. For many liposome formulations, lipid mixtures as in this example are in any case more suitable for stable vesicle formation than the use of an individual lipid component. In the examples below, a mixture of bi-layer-forming lipid (e.g. DPPC, DOPC, DMPC), cholesterol and stearylamine was always used.

The lipid-containing organic phase (98 mg of DPPC/ml of ethanol) is fed into the polar phase flowing past (16 mg of rh-SOD/ml of PBS) in a cross-flow module via a hole having a diameter of 250 µm at a pressure of 1.5 bar without a pump by means of pressure superposition from the nitrogen gas cylinder and the vesicle dispersion formed is transferred to the collecting container. Silicone tubes are used as transport pipes for the polar and for the lipid-containing phase. The internal diameter of the tube for transporting the polar phase from the storage container to the cross-flow module and from the cross-flow module to the storage container is 10 mm and that for transporting the lipid phase from the intermediate container to the cross-flow module is 1.6 mm. A peristaltic pump of the type Ismatec SA 0702 is used as the pump for transporting the polar phase, and 999 is chosen as the pump setting (cf. FIG. 13), corresponding to a pump delivery of 2600 ml/min at the diameter of 10 mm used; the lipid-containing phase is transported to the cross-flow module, preferably without a pump, by a pressure superposition by means of compressed air or inert gas, in this example by means of nitrogen gas.

In the supernatant of the preparation, 14 to 14.5 mg of rh-SOD/ml are measured. Accordingly, 150 to 200 mg of rh-SOD have been enclosed in the liposomes. This corresponds to a degree of inclusion of 9.5–12.5% of the amount of rh-SOD originally dissolved in PBS. Analogous comparative experiments with DOPC (dioleoylphosphatidylcholine) and DMPC (dimyristoylphosphatidylcholine) have given very similar results (results not shown).

EXAMPLE 2

Comparison of One-Stage Process (Without Recirculation) and Process with Recirculation The procedure is that according to Example 1, and any differences are shown in Table 1 below. The experimental arrangement for the recirculation process corresponds to the apparatus which is shown schematically in FIG. 3, and that for the one-stage process corresponds to the apparatus according to FIG. 2. The results are shown in Table 1 and FIG. 4.

TABLE 1

Comparison of the vesicle size distribution in the one-stage and recirculating process

| | Percent [%] of all vesicles in | |
|---|---|---|
| Vesicle size range [nm] | PR* with recirculation | PR* without recirculation ("one-stage") |
| 0 | 0 | 0 |
| 0–100 | 6 | 10.48 |
| 100–200 | 64.11 | 60.78 |
| 200–350 | 20.83 | 22.64 |
| 350–500 | 7.91 | 5.09 |
| 500–650 | 1.45 | 1.12 |
| 650–800 | 0.14 | 0.38 |
| 800– | 0.18 | 0.3 |
| Lipid phase | | |
| Lipid | 10 µmol of DPPC/1 ml of polar phase | |
| Hole | 250 µm | |
| Metering | Pressure superposition with nitrogen | |
| Metering pressure | 1.6 bar | 1.5 bar |
| Flow rate | 75 ml/min | |
| Polar phase | | |
| Solvent | PBS | |
| Tube | Silicone; 6 mm internal diameter | |
| Flow rate | 1000 ml/min | 950 ml/min |

*PR = Process

It is found that the size distribution is virtually identical in both cases, more than 60% of all vesicles formed having a diameter of 100 to 200 nm.

EXAMPLE 3

Influence of the Metering Pressure of the Lipid-containing Phase on Size and Size Distribution of the Lipid Vesicles Example 1 is repeated without rh-SOD and with the following modifications: In contrast to Example 1, the polar phase is recirculated. The lipid phase contains altogether 1470 mg of DPPC, corresponding to 20 µmol of DPPC (molecular weight of DPPC=734) per 1 ml of polar phase. Metering pressure of 1.2 and 2.4 bar and 2.5 and 4.5 bar for the lipid-containing phase are compared with one another.

TABLE 2

Comparison of the vesicle size distribution of liposome batches (20 µmol of lipid/ml of polar phase) with different metering pressures

| Vesicle size range | Percent [%] of all vesicles at | |
|---|---|---|
| [nm] | 1.2 bar | 2.4 bar |
| 0 | 0 | 0 |
| 0–100 | 2.89 | 4.95 |
| 100–200 | 26.8 | 47 |
| 200–350 | 19.73 | 21.03 |
| 350–500 | 21.21 | 15.19 |
| 500–650 | 11.86 | 6.55 |
| 650–800 | 8.26 | 3.14 |
| 800– | 10.1 | 3.16 |

In this and all other experiments described herein, the vesicle sizes were determined by means of flow cytometry, adapted according to Vorauer-Uhl et al. (Cytometrie [Cytometry] 39(2):166–71, 2000). The results are shown in Tables 2 and 2a and in FIGS. 5 and 5A.

TABLE 2a

Comparison of the vesicle size distribution of liposome batches
(20 μmol of lipid/ml of polar phase) with different metering
pressures

| Vesicle size range | Percent [%] of all vesicles at | |
| --- | --- | --- |
| [nm] | 2.5 bar | 4.5 bar |
| 0 | 0 | 0 |
| 0–100 | 25.86 | 82.19 |
| 100–200 | 53.62 | 10.64 |
| 200–300 | 11.66 | 3.05 |
| 300–400 | 3.2 | 1.15 |
| 400–500 | 1.52 | 0.67 |
| 500– | 4.14 | 2.30 |

EXAMPLE 4

Influence of the Metering Pressure of the Lipid-containing Phase on Size and Size Distribution of the Lipid Vesicles Example 1 is repeated without rh-SOD and with the following modifications: In contrast to Example 1, the polar phase is recirculated. Three experimental batches of the same lipid concentration are compared with one another, metering pressures of 0.3, 1.2 and 2.0 bar being tested for the feeding of the lipid-containing phase into the polar phase. The polar phase contains in each case a constant 200 ml of PBS, the lipid phase contains in each case 1470 mg of DPPC in 15 ml of ethanol (92% by volume), corresponding to 10 μmol of DPPC (molecular weight of DPPC=734) per 1 ml of polar phase. In this example, the lipid-containing phase is transported with the aid of a gear pump of the type Gather P 15133. The results are shown in Table 3 and in FIG. 6.

TABLE 3

Size comparison of the vesicles from liposome batches (10 μmol
of lipid/ml of polar phase) produced using metering pressures of
0.3, 1.2 and 2.0 bar

| Vesicle size range | Percent [%] of all vesicles at | | |
| --- | --- | --- | --- |
| [nm] | 0.3 bar | 1.2 bar | 2.0 bar |
| 0 | 0 | 0 | 0 |
| 0–100 | 5.49 | 5.96 | 11.21 |
| 100–200 | 40.39 | 65.61 | 60.75 |
| 200–350 | 18.75 | 15.5 | 15.22 |
| 350–500 | 14.46 | 8.84 | 8.74 |
| 500–650 | 8.83 | 2.97 | 2.89 |
| 650–800 | 5.78 | 0.81 | 0.88 |
| 800– | 7.25 | 0.79 | 0.95 |
| Flow rate (lipid phase) | 11 ml/min | 23 ml/min | 31 ml/min |
| Flow rate (polar phase) | 2700 ml/min | 2700 ml/min | 2700 ml/min |
| Total volume of the polar phase | 200 ml | 200 ml | 200 ml |
| Test duration | 82 sec | 39 sec | 29 sec |

EXAMPLE 5

Comparison of Vesicle Sizes from Experimental Batches with Different Lipid Concentration Example 1 is repeated without rh-SOD and with the following modifications: The lipid-containing phase contains 734, 1470 or 2940 mg of DPPC, corresponding to the calculated concentrations of 5, 10 and 20 μmol of DPPC per 1 ml of polar phase. The results are shown in Table 4 and FIG. 7.

TABLE 4

Vesicle size comparison of liposome batches with different lipid
concentration

| Vesicle size range | Percent [%] of all vesicles at | | |
| --- | --- | --- | --- |
| in [nm] | 5 μmol lipid/ml | 10 μmol lipid/ml | 20 μmol lipid/ml |
| 0 | 0 | 0 | 0 |
| 0–100 | 78.37 | 8.96 | 2.89 |
| 100–200 | 8.6 | 58.9 | 26.8 |
| 200–350 | 5.84 | 18.22 | 19.73 |
| 350–500 | 3.14 | 10.46 | 21.21 |
| 500–650 | 1.96 | 2.7 | 11.86 |
| 650–800 | 1.68 | 0.9 | 8.26 |
| 800– | 2.06 | 0.63 | 10.1 |

EXAMPLE 6

Reproducibility of the Size Distributions of Lipid Vesicles

Figure 8:
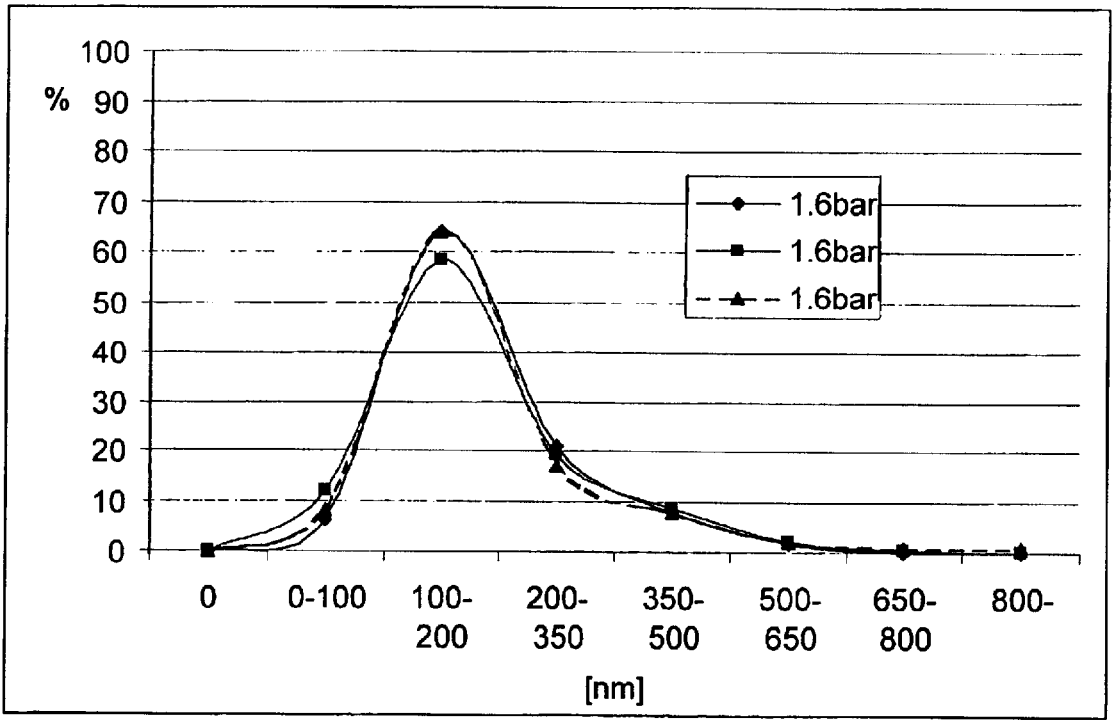
FIG. 8 shows the reproducibility of the vesicle size distribution under constant conditions for three experimental series (ordinate: percent of lipid vesicle population; abscissa: diameter of the lipid vesicles in nm)

Table 5 and FIG. 8 show three separate vesicular preparations which were produced under identical conditions and in which virtually the same size distributions of the lipid vesicles are present. The vesicular preparations were produced according to Example 1, but without rh-SOD; any deviations therefrom are shown in Table 5 below. In contrast to Example 1, the polar phase is recirculated.

TABLE 5

Reproducibility of the size distribution of lipid vesicles (metering
pressure 1.6 bar)

| Vesicle size range | Percent [%] of all vesicles | | |
| --- | --- | --- | --- |
| | Preparation 1 | Preparation 2 | Preparation 3 |
| 0–100 | 6 | 12 | 8.17 |
| 100–200 | 64.11 | 58.33 | 63.92 |
| 200–350 | 20.83 | 19.3 | 17.24 |
| 350–500 | 7.91 | 8.43 | 7.77 |
| 500–650 | 1.45 | 1.93 | 1.91 |
| 650–800 | 0.14 | 0.38 | 0.7 |
| 800– | 0.18 | 0.13 | 0.83 |
| Lipid phase | | | |
| EtOH | 92% by volume | | |
| Lipid metering | 10 μmol of DPPC per 1 ml of polar phase | | |
| Metering method | $N_2$ gas | $N_2$ gas | Pump* |
| Hole | 250 μm | | |
| Flow rate | 75 ml/min | 75 ml/min | 75 ml/min |
| Polar phase | | | |
| Carrier medium | PBS | | |
| Flow rate | 2700 ml/min | | |
| Amount | 200 ml | 200 ml | 200 ml |
| Duration | 12 sec | 12 sec | 12 sec |

*Gear pump mode Gather P15133

EXAMPLE 7

Modified One-stage Process with Increased Metering Volume of the Lipid Phase and Subsequent Dilution of the Vesicle Dispersion Formed Example 1 is repeated with the following modifications: Using an apparatus according to FIG. 2, two parts by volume (200 ml) of the polar phase (PBS) are initially introduced into the collecting container and one part by volume (100 ml) of PBS is initially introduced into the storage container. 1600 mg of rh-SOD are dissolved in the 100 ml of PBS in the storage container. Three times the amount of lipid (2205 mg of lipid)—in comparison with Example 1—is now dissolved in three times the amount (22.5 ml) of ethanol concentration: 92% by volume). The flow rate of the polar phase is controlled so that the total amount of lipid/ethanol solution is introduced into the one-part by volume (100 ml) of the polar phase. The phase dispersion forming in the cross-flow module is passed on into the collecting container, where the excess of ethanol is immediately compensated by the initially introduced polar solvent PBS. By means of this process, 450 to 600 mg of rh-SOD are enclosed in the lipid vesicle. This corresponds to an incorporation rate of 28 to 38%, based on the total amount of initially introduced rh-SOD.

Thus, by means of this process variant, about 3 times the amount of protein in comparison with the process according to Example 1 is enclosed. The vesicle size distribution achieved by means of this process is shown in Table 6 below and in FIG. 9. As is evident from FIG. 9, the size distribution of the lipid vesicles which is obtained by this preparation technique surpasses even that of the unmodified one-stage process with respect to the homogeneity and the fraction of vesicles having a diameter in the range of 100–200 nm.

TABLE 6

Comparison of the vesicle size distribution in the one-stage process with normal and increased metering volume of the lipid phase per volume of the polar phase

| Vesicle size range | Percent [%] of all vesicles | |
| --- | --- | --- |
|  | normal | three-fold concentration |
| 0 | 0 | 0 |
| 0–100 | 8.96 | 14.02 |
| 100–200 | 58.9 | 71.31 |
| 200–350 | 18.22 | 9.5 |
| 350–500 | 10.46 | 3.28 |
| 500–650 | 2.7 | 1.22 |
| 650–800 | 0.9 | 0.52 |
| 800– | 0.63 | 0.75 |
| Lipid phase | | |
| Lipid | 10 μmol of DPPC per 1 ml of polar phase (based on the total amount of polar phase initially introduced in the storage container and collecting container at the start) | |
| Hole | 250 μm | |
| Metering | Pressure superposition with nitrogen gas | |
| Metering pressure | 2.4 bar | |
| Polar phase | | |
| Carrier medium | PBS | |
| Tube | Silicone; 6 mm internal diameter | |
| Flow rate | 400 ml/min | |

EXAMPLE 7a

Figure 9A:
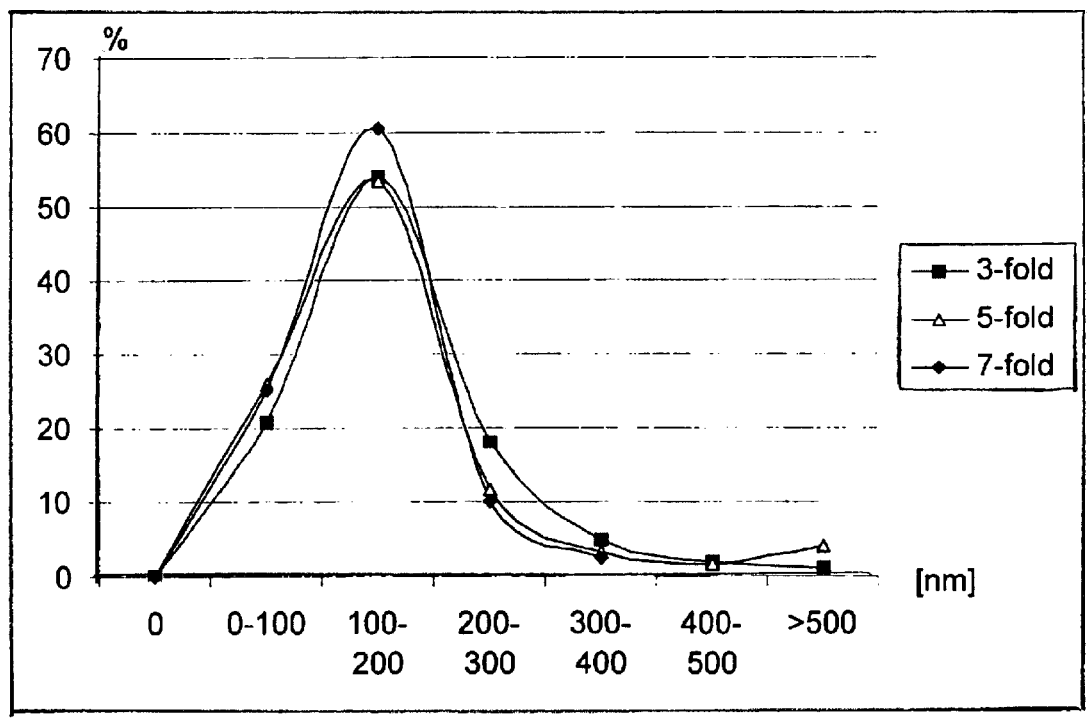
FIG. 9A shows a comparison of the size distribution of the lipid vesicles between three processes with increased mixing ratio (metered volume of the lipid phase per unit volume of the polar phase) and subsequent dilution of the phase dispersion (ordinate: percent of lipid vesicle population; abscissa: diameter of the lipid vesicles in nm)

Modified One-stage Process with Increased Metering Volume of the Lipid Phase and Subsequent Dilution of the Vesicle Dispersion Formed Example 1 is repeated with the following modifications: Using an apparatus according to FIG. 2, two, four or six parts by volume (200 ml, 400 ml or 600 ml) of the polar phase (PBS) are initially introduced into the collecting container and one part by volume (100 ml) of PBS is initially introduced into the storage container. 1600 mg of rh-SOD are dissolved in the 100 ml of PBS in the storage container. Three, five or seven times the amount of lipid (2205, 3670 and 5138 mg, respectively, of lipid)—in comparison with Example 1—is now dissolved in three, five or seven times the amount (22.5, 37.5 and 52.5 ml) of ethanol (concentration: 92% by volume). The flow rate of the polar phase is controlled so that the total amount of lipid/ethanol solution is introduced into the one part by volume (100 ml) of the polar phase. The phase dispersion forming in the cross-flow module is passed on into the collecting container, where the excess of ethanol is immediately compensated by the initially introduced polar solvent PBS. By means of this process, 450 to 600 mg (with 3 times the amount of lipid), 640 to 720 mg (with 5 times the amount of lipid) or 880 to 960 mg (with 7 times the amount of lipid) of rh-SOD are enclosed in the lipid vesicles. This corresponds to an incorporation rate of 28 to 38%, based on the total amount of initially introduced rh-SOD, or 40 to 45% in the case of 5-fold metering and 55 to 60% in the case of 7-fold metering. Thus, by means of this process variant, about 3, 5 or 7 times the amount of protein is enclosed in comparison with the process according to Example 1. The vesicle size distribution achieved by means of this process is shown in Table 6a below and in FIG. 9A.

TABLE 6a

Comparison of the vesicle size distribution in the one-stage process with normal and increasing metering volume of the lipid phase per volume of the polar phase

| Vesicle size range | Percent of all vesicles at | | |
| --- | --- | --- | --- |
| [nm] | 3 times | 5 times | 7 times |
| 0 | 0 | 0 | 0 |
| 0–100 | 20.8 | 25.86 | 25.26 |
| 100–200 | 53.93 | 53.62 | 60.57 |
| 200–300 | 18.09 | 11.66 | 9.9 |
| 300–400 | 4.99 | 3.20 | 2.35 |
| 400–500 | 1.98 | 1.52 | 1.27 |
| 500– | 1.15 | 4.14 | 1.48 |
| Lipid phase | | | |
| Lipid | 10 μmol of DPPC per 1 ml of polar phase (based on the total amount of polar phase initially introduced into storage container and collecting container at the start) | | |
| Hole | 250 μm and 500 μm | | |
| Metering | Pressure superposition with nitrogen gas | | |
| Metering pressure | 2.5 bar | | |
| Polar phase | | | |
| Carrier medium | PBS | | |
| Tube | Silicone; 6 mm internal diameter | | |
| Flow rate | 400 ml/min | | |

EXAMPLE 8

Comparison of the Vesicle Size Distribution as a Function of the Size of the Hole in the Cross-flow Module Example 1 is repeated without rh-SOD; any deviations therefrom are shown in Table 7 below. In contrast to Example 1, the polar phase is recirculated. The results are shown in FIG. 10 and in Table 7.

TABLE 7

Vesicle size comparison with the use of cross-flow modules with different hole diameters

| | Percent [%] of all vesicles at a hole diameter of | |
|---|---|---|
| Vesicle size range | 150 μm | 250 mm |
| 0 | 0 | 0 |
| 0–100 | 5.96 | 6.3 |
| 100–200 | 65.61 | 67.01 |
| 200–350 | 15.5 | 16.34 |
| 350–500 | 8.84 | 7.47 |
| 500–650 | 2.97 | 2 |
| 650–800 | 0.81 | 0.67 |
| 800– | 0.79 | 0.74 |
| Lipid phase | | |
| Lipid | 10 μmol of DPPC/ml of polar phase | |
| Hole | 150 μm | 250 μm |
| Metering | Gear pump type Gather P15133 | |
| Metering pressure | 1.2 bar | |
| Flow rate | 23 ml/min | 67 ml/min |
| Polar phase | | |
| Carrier medium | PBS | |
| Tube | Silicone; 10 mm internal diameter | |
| Flow rate | 2700 ml/min | |

The results show that the diameter of the metering orifice in the cross-flow module, at least in the range of the diameters tested, appears to have no significant influence on the size and on the size distribution of the lipid vesicles produced. Further experiments have shown that in particular holes having diameters in the range from 50 to 1500 μm appear to be suitable for the purposes of the present invention. Smaller hole diameters are mechanically difficult to produce and are therefore less suitable.

EXAMPLE 9

Comparison of the Vesicle Size Distribution on the 0.3 and 2.5 Litre Scales

Example 7 is repeated, 300 ml of polar phase (as in Example 7) being used in a first experimental batch and 2500 ml of polar phase being used in a second experimental batch, under otherwise identical conditions. The lipid and ethanol concentrations correspond to those which are mentioned in Example 7, the liquid volume of the ethanolic liquid phase in the 2500 ml experimental batch of course also being higher by the same factor, i.e. 187.5 ml).

TABLE 8

Vesicle size distribution on scale-up

| | Percent [%] of all vesicles | |
|---|---|---|
| Vesicle size range | 0.3 litre | 2.5 litres |
| 0 | 0 | 0 |
| 0–100 | 14.02 | 7.18 |
| 100–200 | 71.31 | 73.51 |
| 200–350 | 9.5 | 10.16 |
| 350–500 | 3.28 | 6.14 |
| 500–650 | 1.22 | 1.24 |
| 650–800 | 0.52 | 0.84 |
| 800– | 0.75 | 0.93 |

TABLE 8-continued

Vesicle size distribution on scale-up

| | Percent [%] of all vesicles | |
|---|---|---|
| Vesicle size range | 0.3 litre | 2.5 litres |
| Lipid phase | | |
| Lipid | 10 μmol of DPPC per 1 ml of polar phase (based on the total amount of polar phase initially introduced into the storage container and collecting container at the start) | |
| Hole | 250 μm | |
| Metering | Pressure superposition with nitrogen gas | |
| Metering pressure | 2.4 bar | |
| Polar phase | | |
| Carrier medium | PBS | |
| Tube | Silicone; 6 mm internal diameter | |
| Flow rate | 400 ml/min | |

EXAMPLE 10

Determination of Pressure/flow Rate Curves for the Liquid Phases

In order to be able to tailor the liquid streams of the polar and of the ethanolic lipid phase to one another, corresponding flow rate or pressure/flow rate curves were determined with the pumps used and were plotted in the form of graphs. On the one hand, a peristaltic pump, Ismatec SA 0702 model (for transporting the polar phase) and, on the other hand, a gear pump, Gather P15133 model (for transporting the ethanolic lipid phase), were used. Alternatively, pump-free pressure superposition with nitrogen was used for transporting the ethanolic lipid phase.

a) Plotting a Pressure/flow Rate Curve for the Ethanol Phase

Figure 12:
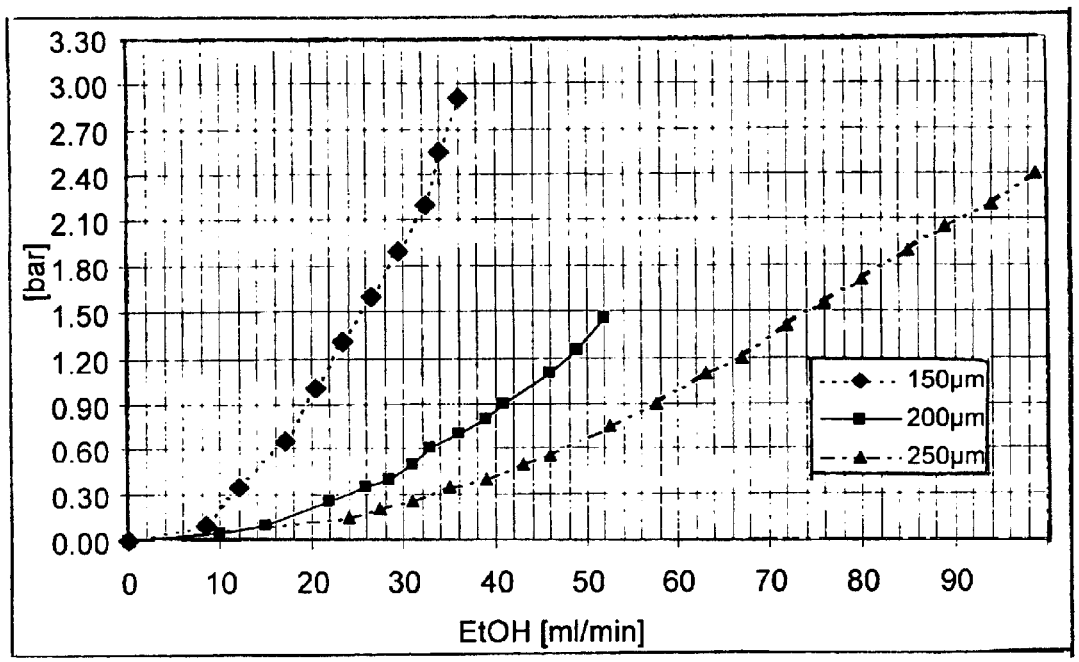
FIG. 12 shows flow/pressure curves of 92% by volume of ethanol at 55° C. with the use of a cross-flow module with holes of 150, 200 and 250 $\mu$m diameter.

The values determined for the gear pump are listed in Table 9 below and plotted in the form of a graph in FIG. 12.

The flow rate (volume flow) of ethanol (92% by volume) at a temperature of 45–55° C. through the feed pipe for the lipid phase or through the subsequent hole in the cross-flow module was measured. A silicone tube having an internal diameter 1.6 mm was used as the feed pipe from the pump to the cross-flow module. Three cross-flow modules, each having only a single hole, were used, the holes having nominal diameters of 150 μm, 200 μm or 250 μm.

After it had been found that the lipid-containing phase can be transported at least just as accurately and uniformly into the cross-flow module by means of pressure superposition of the intermediate container (according to FIG. 2 and FIG. 3) using compressed air or nitrogen gas, this pump-free method was also used for the production process according to the invention, as a simple and maintenance-free alternative for transportation by means of a gear pump.

b) Plotting a Flow Rate Curve for the Polar Phase

The polar phase used was PBS. The pump used was a peristaltic pump of the type Ismatec SA 0702, and a silicone tube was used as a feed pipe from the pump to the cross-flow module. Three different tube diameters were tested: 6, 8 and 10 mm internal diameter. The tubes were filled in the absence of bubbles. The data for the pump setting are based on the scale present on the pump and intended for selection of the pump delivery. The values determined are shown below in Table 10 and in FIG. 13.

TABLE 9

Pressure/flow rate curve for ethanolic phase

| Flow rate [ml/min] | Metering pressure [bar] at a hole diameter of | | |
|---|---|---|---|
| | 150 μm | 200 μm | 250 μm |
| 0.00 | 0.00 | 0.00 | 0.00 |
| 8.50 | 0.10 | | |
| 10.00 | | 0.05 | |
| 12.00 | 0.35 | | |
| 15.00 | | 0.10 | |
| 17.00 | 0.65 | | |
| 20.50 | 1.00 | | |
| 22.00 | | 0.25 | |
| 23.50 | 1.30 | | |
| 24.00 | | | 0.15 |
| 26.00 | | 0.35 | |
| 26.50 | 1.60 | | |
| 27.50 | | | 0.20 |
| 28.50 | | 0.40 | |
| 29.50 | 1.90 | | |
| 31.00 | | 0.50 | 0.25 |
| 32.50 | 2.20 | | |
| 33.00 | | 0.60 | |
| 34.00 | 2.55 | | |
| 35.00 | | | 0.35 |
| 36.00 | 2.90 | 0.70 | |
| 39.00 | | 0.80 | 0.40 |
| 41.00 | | 0.90 | |
| 43.00 | | | 0.50 |
| 46.00 | | 1.10 | 0.55 |
| 49.00 | | 1.25 | |
| 52.00 | | 1.45 | |
| 52.50 | | | 0.75 |
| 57.50 | | | 0.90 |
| 63.00 | | | 1.10 |
| 67.00 | | | 1.20 |
| 72.00 | | | 1.4 |
| 76.00 | | | 1.55 |
| 80.00 | | | 1.7 |
| 85.00 | | | 1.9 |
| 89.00 | | | 2.05 |
| 94.00 | | | 2.2 |
| 99.00 | | | 2.4 |

TABLE 10

Calibration curve for PBS flow rates by means of peristaltic pump

| Pump setting | Flow rate [ml/min] | | |
|---|---|---|---|
| | 6 mm ID* | 8 mm ID* | 10 mm ID* |
| 0 | 0 | 0 | 0 |
| 100 | 100 | 170 | 250 |
| 200 | 200 | 360 | 470 |
| 300 | 310 | 550 | 740 |
| 400 | 415 | 710 | 980 |
| 500 | 520 | 890 | 1220 |
| 600 | 625 | 1120 | 1460 |
| 700 | 730 | 1300 | 1800 |
| 800 | 840 | 1510 | 2040 |
| 900 | 950 | 1700 | 2320 |
| 1000 | 1060 | | 2600 |

*ID = Internal diameter

What is claimed is:

1. Apparatus for the production of lipid vesicles, which comprises the following components: a pipe (1) which is hollow in the interior and is intended for transporting a polar liquid phase, a pipe (2) which is hollow in the interior and is intended for transporting a lipid-containing organic liquid phase, a collecting container (7) for receiving lipid vesicles produced, and means for transporting the liquid phases through the pipes (1) and (2), characterized in that the pipe (1) is connected to the pipe (2) via a common, liquid-permeable orifice (3), the common orifice (3) being arranged so that the organic liquid phase from the pipe (2) can pass through the orifice (3) substantially perpendicularly to the direction of flow of the polar liquid phase flowing in pipe (1) and can enter, preferably in the form of a spray mist, the polar liquid phase flowing past the orifice (3), and furthermore the pipes (1) and (2) in the region of the common orifice (3) being free of means generating turbulences or shear forces.

2. Apparatus according to claim 1, characterized in that the pipes (1) and (2) in the region of the common orifice (3) are free of obstacles or stirring or dispersing aids generating turbulences or shear forces.

3. Apparatus according to claim 1, characterized in that the diameter of the orifice (3) is smaller than the internal diameter of the pipes (1) and (2) and is preferably in the range of 50–1500 μm.

4. Apparatus according to claim 1, characterized in that the pipes (1) and (2) are arranged either parallel or intersecting one another in the region of the common orifice (3), or that the pipe (2) is adjacent one end face, preferably in a T-shaped manner, to the outer wall of the pipe (1).

5. Apparatus according to claim 1, characterized in that the pipes (1) and (2) are produced from chemically and mechanically resistalt material, in particular from stainless steel or a suitable rigid plastic, at least in the region of the common orifice (3).

6. Apparatus according to claim 1, characterized in that the pipes (1) and (2) are formed as a prefabricated unit in the region of the common orifice (3), in particular as cross-flow module (4).

7. Apparatus according to claim 1, characterized in that a pipe (1') branches out from the pipe (1) downstream of the orifice (3) and, in the region of the branch or downstream thereof, the pipe (1) contains a controllable gate (15) with the aid of which at least a part of the liquid stream can be deflected from the pipe (1) into the pipe (1').

8. Apparatus according to claim 1, characterized in that the means for transporting the liquid phases comprise a pump (6) which is arranged in the pipe (1) between storage container (5) and orifice (3) and transports the polar liquid phase out of the storage container (5) through the pipe (1) in the direction of the contact area with the orifice (3) and further into the collecting container (7) and/or via a pipe (1') at least partly back into the storage container (5).

9. Apparatus according to claim 1, characterized in that the means for transporting the liquid phases comprise a pump (9) with the aid of which the lipid-containing phase is transported from a storage container (8), optionally via a filter (10), into an intermediate container (11), and optionally further through the pipe (2) and the orifice (3) into the pipe (1).

10. Apparatus according to claim 1, characterized in that the means for transporting the liquid phases comprise a pressure source (13) which is connected to an intermediate container (11), optionally via an intermediate filter (12), and which permits pump-free transport of the lipid-containing phase from the intermediate container (11) via the pipe (2) through the orifice (3) by means of pressure superposition by compressed air or an inert gas under pressure.

11. Apparatus according to claim 1, characterized in that it comprises or more pipes (1) and/or two or more pipes (2) which have two or more common orifices (3).

12. Process for the production of lipid vesicles having a controllable size distribution by pressure-controlled metering of lipid-containing liquid phase into a flowing polar liquid phase with the use of an apparatus according to claim 1, the polar liquid phase being transported through a pipe which contains at least at one point of its side wall, an orifice through which the lipid-containing liquid phase is forced under pressure and in a direction substantially perpendicular to the direction of flow of the polar liquid phase and is metered, in particular sprayed, into the polar liquid phase flowing past the orifice, lipid vesicles having a narrow size distribution forming—spontaneously and without the action of mechanical stirring or dispersing aids—by a controllable self-assembly effect.

13. Process according to claim 12, in which the polar liquid phase has laminar or virtually laminar flow before reaching the side wall orifice.

14. Process according to claim 12, in which the lipid-containing liquid phase is metered at a pressure of 0.1 to 15, bar through the orifice into the polar liquid phase flowing past.

15. Process according to claim 12, in which the lipid-containing liquid phase is metered in an amount of 1–100 μmol, of lipid per 1 ml of polar liquid phase, based on the total amount of polar phase used.

16. Process according to claim 15, in which only a part of the total polar liquid phase is transported through the pipe to the orifice and—after loading with lipid-containing liquid phase—is transported further as concentrated vesicle dispersion to a collecting container, while the remaining part of the polar liquid phase is used for diluting the concentrated vesicle dispersion and is preferably initially introduced into the collecting container.

17. Process according to claim 12, in which the lipid-containing liquid phase contains ethanol as a solvent and is metered into the polar liquid phase in an amount which gives a final concentration of not more than 10% by volume, of ethanol in the polar liquid phase.

18. Process according to claim 12, in which at least a part of the polar liquid phase is recirculated after loading with lipid-containing liquid phase and is fed for further loading with lipid-containing liquid phase.

19. Process according to claim 12, in which the polar liquid phase and/or the lipid-containing liquid phase contains at least one desired substance, for loading the lipid vesicles.

20. Process according to claim 12, in which at least 60% of the lipid vesicles forming have a diameter of 100 to 350 nm.

21. The process of claim 14 wherein said pressure is 0.3–5 bar.

22. The process of claim 15 wherein said amount is 2.5–25 μmol.

23. The process of claim 16 wherein said part is 10–50% by volume.

24. The process of claim 17 wherein said concentration is not more than 7.5% by volume.

25. The process of claim 19 wherein said substance is a pharmaceutically active substance.

* * * * *